United States Patent [19]
Yoneda et al.

[11] Patent Number: 5,576,109
[45] Date of Patent: Nov. 19, 1996

[54] SURFACE TREATING AGENT AND SURFACE-TREATED SUBSTRATE

[75] Inventors: Takashige Yoneda; Takeshi Morimoto; Fumiaki Gunji; Kenji Ishizeki; Yukiko Ono, all of Yokohama, Japan

[73] Assignee: Asahi Glass Company Ltd., Tokyo, Japan

[21] Appl. No.: 425,037

[22] Filed: Apr. 18, 1995

[30] Foreign Application Priority Data

Apr. 20, 1994 [JP] Japan ..................................... 6-81627
May 11, 1994 [JP] Japan ..................................... 6-97719

[51] Int. Cl.$^6$ ..................................................... B32B 25/20
[52] U.S. Cl. ............................... 428/447; 528/33; 528/34; 528/42
[58] Field of Search ................... 528/34, 33, 42; 428/447

[56] References Cited

U.S. PATENT DOCUMENTS

| | | | |
|---|---|---|---|
| 4,727,127 | 2/1988 | Suzuki | 528/34 |
| 4,731,411 | 3/1988 | Lucas | 528/34 |
| 4,895,918 | 1/1990 | Lucas | 528/34 |
| 5,264,484 | 11/1993 | Arai et al. | 528/34 |
| 5,371,164 | 12/1994 | Kobayashi et al. | 528/34 |

*Primary Examiner*—Ralph H. Dean
*Attorney, Agent, or Firm*—Oblon, Spivak, McClelland, Maier & Neustadt, P.C.

[57] ABSTRACT

A surface treating agent containing a silicone compound of the formula (A):

$$(R^1)_a(R^2)_b(Z^1)_{3-a-b}SiO\text{—}[Si(R^3)_c(R^4)_d(Z^2)_{2-c-d}O]_n\text{—}Si(R^5)_e(R^6)_f(Z^3)_{3-e-f} \quad (A)$$

wherein each of $R^1$ to $R^6$ which are independent of one another, is a hydrogen atom or an organic group, provided that at least one of $R^1$ to $R^6$ is an organic group;

each of $Z^1$ to $Z^3$ which are independent of one another, is an isocyanate group or a hydrolyzable group;

each of a to f which are independent of one another, is an integer of 0, 1 or 2, provided $1 \leq a+b \leq 3$, $0 \leq c+d \leq 2$, $1 \leq e+f \leq 3$ and $2 \leq a+b+c+d+e+f \leq 7$; and n is an integer of 0 or at least 1.

18 Claims, 2 Drawing Sheets

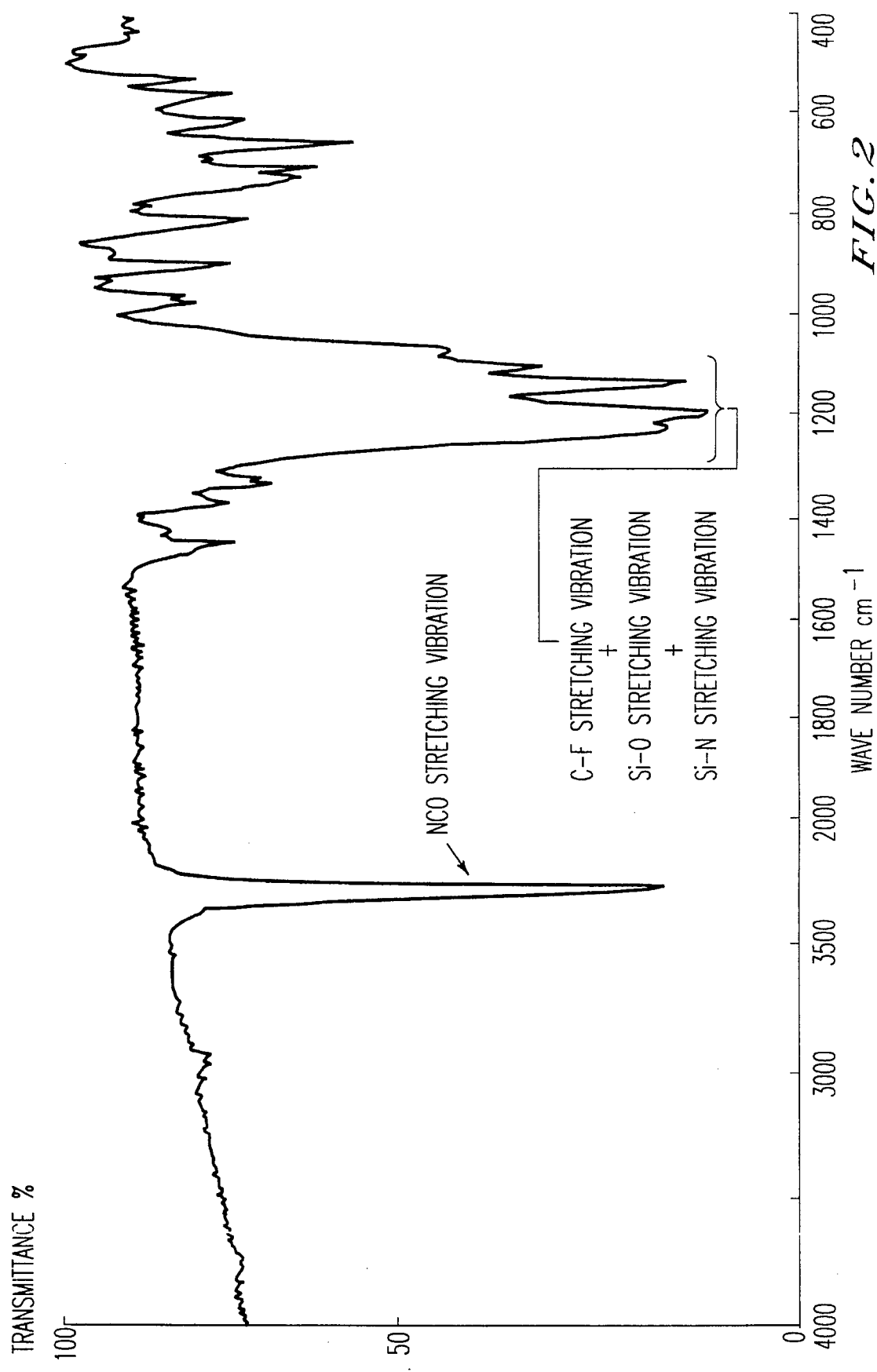

SURFACE TREATING AGENT AND SURFACE-TREATED SUBSTRATE

The present invention relates to a novel surface treating agent for normal temperature treatment and a substrate treated with such a surface treating agent. Particularly, it relates to a surface treating agent which is capable of imparting excellent water repellency and antifouling properties to the surface of a substrate made of e.g. glass, plastic, ceramics or metal, and a substrate treated with such a surface treating agent.

Substrates made of various materials and various substrates having treated surface layers are used in various fields. However, adverse effects brought by dusts, oil stains or water deposited on the surface of such substrates are problematic.

For example, in transportation equipments such as electric cars, automobiles, ships or aircrafts, the surface of an exterior part such as an outer panel, a window glass, a mirror or a display surface material, an interior part such as an instrument panel, or other articles, is desired to be always clean. If raindrops, dusts or soils are deposited on the surface, or if moisture is condensed thereon by an influence of the temperature or humidity in air, the outer appearance will be impaired. If such a surface is a surface which is directly visually observed or which is directly touched by a person, it may give a filthy impression or may create a hygienic problem.

Further, a stain on an article for a transportation equipment may bring about a deterioration of the function of the article. Especially in a case where the article for the transportation equipment is an article for which transparency or a see-through property is required (such as a window glass or a mirror), a deterioration of the transparency or the see-through property may mean that the purpose intended by the article can not be attained, and may cause a serious accident.

Means to remove such dusts, oil stains or water drops (such as removal by wiping off or by means of a wiper) may sometimes impart fine scratch marks on the surface. Further, such scratch marks may sometimes be widened by foreign particles accompanying such dusts, oil stains or water drops. Furthermore, it is well known that when moisture is attached to a glass surface, glass components are likely to elute into the moisture, whereby the surface will be eroded, thus leading to so-called scorching. If the surface is strongly polished or abraded to remove such scorching, a fine roughness is likely to form. At the see-through portion made of glass having substantial scorching or a fine roughness on its surface, its basic function is lowered, and scattering of light on its surface is substantial, whereby it tends to be difficult to secure the field of view, and there will also be a problem from the viewpoint of safety.

Further, dusts, stains or water drops are likely to give a hazardous influence to the surface of an article for a transportation equipment and to promote damages, soiling, yellowing or corrosion. Otherwise they may induce a change in the electrical characteristics, the mechanical properties or the optical properties of the article for a transportation equipment. Adverse effects of this type are problematic not only in the field of articles for transportation equipments but also in various fields including articles for building or building decoration or articles for electric or electronic equipments.

Under these circumstances, it is strongly desired to develop a technique of imparting to a substrate surface a nature of preventing adhesion of dusts, soils and water drops or a nature whereby attached dusts, stains or water drops can easily be removed (such natures will be referred to hereinafter simply as antifouling properties).

As a method for imparting such antifouling properties, a method has heretofore been proposed wherein a surface treating agent such as silicone wax, silicone oil made of an organopolysiloxane or a surfactant is directly coated on the substrate.

However, conventional surface-treating agents have a drawback that adhesion of the treating agents themselves to the substrates was rather low, and their antifouling properties can not be maintained for a long period of time. Thus, the range of their application has been rather limited.

Further, it is desired to impart such antifouling properties not only to articles to be produced anew but also to articles which have already been used or in which a deterioration in the performance after treatment has been observed. However, to be useful for all of such articles, the surface treating agent must be capable of imparting antifouling properties simply by directly treating such articles with it at a normal temperature. For example, when it is applied to a windshield glass for an automobile which is commercially available, it is practically impossible to replace the windshield glass of each automobile for heat treatment, from the economical reason. Likewise, it is practically impossible to subject the entire automobile to baking after coating. Accordingly, with conventional treating agents, such treatment is difficult or costly.

Accordingly, it is an object of the present invention to provide a surface treating agent whereby treatment can be conducted at a normal temperature and whereby excellent antifouling properties can be imparted.

It is another object of the present invention to provide a substrate which not only has antifouling properties but also is excellent in the abrasion resistance, the chemical resistance and the weather resistance.

The present invention provides a surface treating agent containing a silicone compound of the formula (A) and a substrate treated with such a surface treating agent:

$$(R^1)_a(R^2)_b(Z^1)_{3-a-b}SiO\text{—}[Si(R^3)_c(R^4)_d(Z^2)_{2-c-d}O]_n\text{—}Si(R^5)_e(R^6)_f(Z^3)_{3-e-f} \quad (A)$$

wherein each of $R^1$ to $R^6$ which are independent of one another, is a hydrogen atom or an organic group, provided that at least one of $R^1$ to $R^6$ is an organic group;

each of $Z^1$ to $Z^3$ which are independent of one another, is an isocyanate group or a hydrolyzable group;

each of a to f which are independent of one another, is an integer of 0, 1 or 2, provided $1 \leq a+b \leq 3$, $0 \leq c+d \leq 2$, $1 \leq e+f \leq 3$ and $2 \leq a+b+c+d+e+f \leq 7$; and n is an integer of 0 or at least 1.

In the following description, the compound of the formula (A) will be represented by compound (A).

BRIEF DESCRIPTION OF THE DRAWINGS

In the accompanying drawings:

FIG. 2 is a graph showing the infrared spectrum of the reaction product obtained in Example 1.

Figure 1:
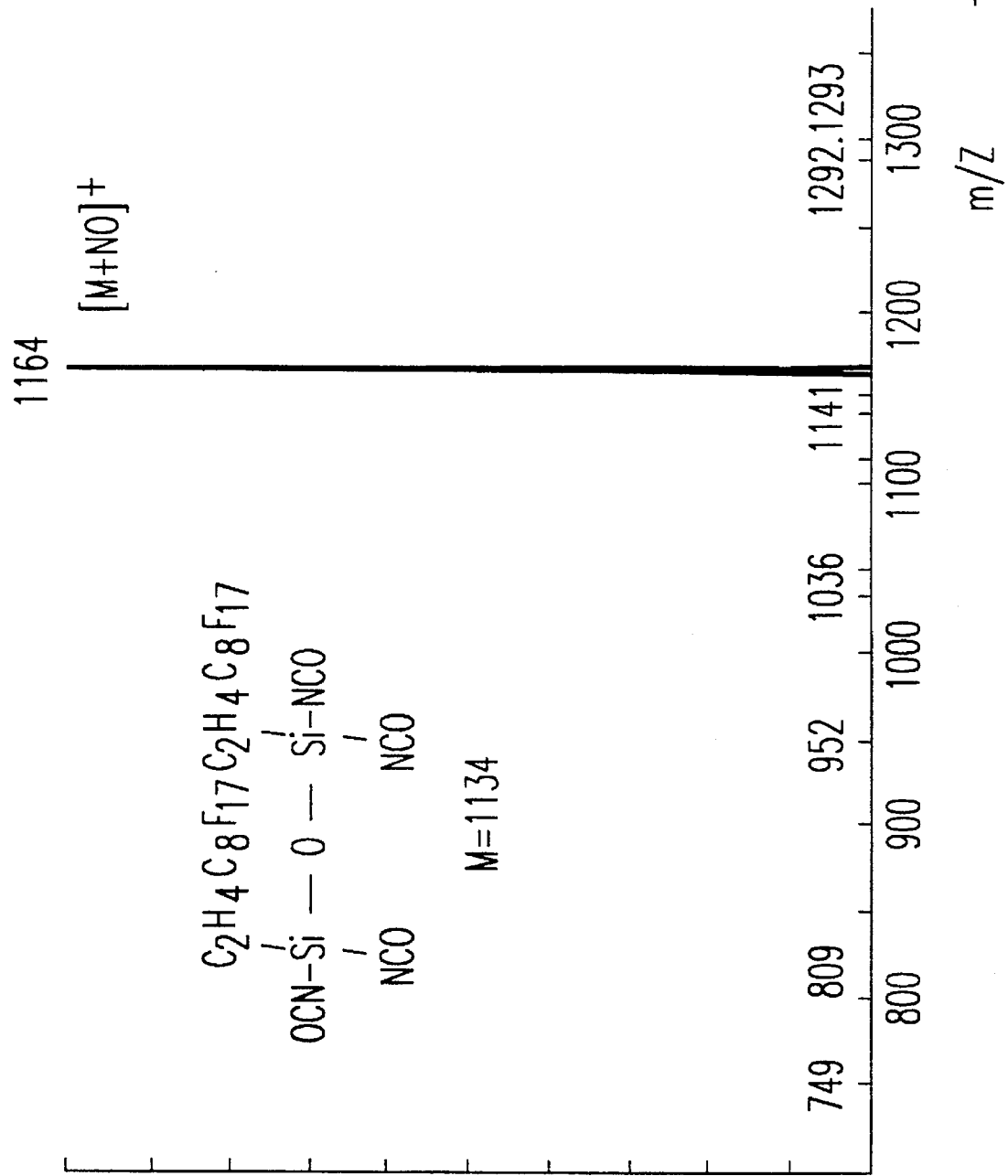
FIG. 1 is a graph showing the mass spectrum of the reaction product obtained in Example 1.

When each of $R^1$ to $R^6$ of compound A is a monovalent organic group, it may be an organic group which includes a halogen atom, a functional group and a connecting group. The organic group is preferably a hydrocarbon group or an organic group containing a halogen atom (hereinafter referred to as a halogenated organic group).

The carbon number of the organic group is preferably from 1 to 30.

The hydrocarbon group may be an aliphatic hydrocarbon group or an aromatic hydrocarbon group. However, an aliphatic hydrocarbon group is preferred. As a monovalent aliphatic hydrocarbon group, an alkyl group, an alkenyl group or a cycloalkyl group is preferred, and an alkyl group is particularly preferred. Specifically, a methyl group, an ethyl group, a propyl group or a butyl group may, for example, be mentioned. As the aromatic hydrocarbon group, an aryl group is preferred.

As the halogen atom in the halogenated organic group, a chlorine atom, a fluorine atom or a bromine atom is preferred. Among them, a chlorine atom or a fluorine atom is more preferred, and a fluorine atom is particularly preferred.

As the halogenated organic group, a halogenated hydrocarbon group is preferred, and a halogenated alkyl group is particularly preferred. The halogenated alkyl group may, for example, be a chloroalkyl group, a fluoroalkyl group or a chlorofluoroalkyl group.

Further, as the halogenated organic group, a polyfluoroorganic group wherein two or more hydrogen atoms in the organic group are substituted by fluorine atoms, is preferred. As such a polyfluoroorganic group, a polyfluorohydrocarbon group is preferred. Particularly preferred is a polyfluorohydrocarbon group wherein two or more hydrogen atoms in the above hydrocarbon group are substituted by fluorine atoms.

As the polyfluorohydrocarbon group, a polyfluoroalkyl group is particularly preferred. The polyfluoroalkyl group is a group wherein two or more hydrogen atoms of an alkyl group are substituted by fluorine atoms. In the following description, such a polyfluoroalkyl group is represented by $R_f$.

The carbon number of $R_f$ is preferably from 3 to 18. $R_f$ may have a straight chain structure or a branched chain structure. The proportion of fluorine atoms in $R_f$ is preferably such that (the number of fluorine atoms in $R_f$)/(the number of hydrogen atoms in an alkyl group having the same carbon number, which corresponds to $R_f$) is at least 60%, more preferably at least 80%.

Further, $R_f$ may contain an ether-type oxygen atom or a sulfur atom. For example, it may be a polyfluorooxaalkyl group or a polyfluorothioalkyl group. As the polyfluorooxaalkyl group, a group containing a polyfluoroethylenoxy moiety, a polyfluoropropylenoxy moiety, a polyfluoroethyloxy moiety or a polyfluoropropyloxy moiety, may, for example, be mentioned. Further, as the polyfluorothioalkyl group, a group containing a polyfluoroethylenethio moiety or a polyfluoropropylenethio moiety, or a group containing a polyfluoroethylthio moiety or a polyfluoropropylthio moiety, may, for example, be mentioned.

$R_f$ is preferably a perfluoroalkyl group wherein all hydrogen atoms in the above $R_f$ are substituted by fluorine atoms, a group having a perfluoroalkyl moiety, or a group having a perfluoroalkylene moiety. The perfluoroalkyl group or the perfluoroalkyl moiety preferably has a carbon number of from 3 to 21, and the perfluoroalkylene moiety preferably has a carbon number of from 2 to 18.

Particularly preferred as $R_f$ is a group having a structure in which the above perfluoroalkyl moiety and the alkylene group are connected. It is particularly preferred that $R_f$ is represented by $C_aF_{2a+1}(CH_2)_b$— wherein a is an integer of from 3 to 21, and b is an integer of from 1 to 6, particularly preferably 2.

Further, each of $R^1$ to $R^6$ of compound A may be an organic group containing a functional group. As the functional group, a hydroxyl group, an amino group, a mercarpto group or a carboxyl group may, for example, be mentioned. The number of functional groups is not paraticularly limited, but in a usual case at a level of 1 or 2, preferably 1.

Further, each of $R^1$ to $R^6$ of compound A may be an organic group containing a connecting group. As the connecting group, a bivalent connecting group is preferred, and particularly preferred is an ester bond, an ether bond, a thioether bond, an imino bond, an amide bond, an urethane bond or a bivalent connecting group containing such a bond.

$R^1$ to $R^6$ of compound A may be the same or different, and each represents a hydrogen atom or the above described organic group, provided that at least one of them is the organic group. The number of organic groups is preferably at least 4. Particularly preferred is a case where all of them are such organic groups.

The organic group preferably contains a hydrophobic organic group. As the hydrophobic organic group, a polyfluoroorganic group or a long chain hydrocarbon group is preferred. As the polyfluoroorganic group, a polyfluorohydrocarbon group is preferred, and particularly preferred is $R_f$.

As the long chain hydrocarbon group, a straight chain hydrocarbon group having at least 6 carbon atoms is preferred, and particularly preferred is an alkyl group having at least 6 carbon atoms.

It is preferred that at least a half of the total number of organic groups in compound A is constituted by hydrophobic organic groups. Particularly preferably, all of the organic groups are hydrophobic groups.

$Z^1$ to $Z^3$ of compound A may be the same or different, and each represents an isocyanate group or a hydrolyzable group. An isocyanate group may sometimes be regarded as a kind of hydrolyzable groups. However, for the purpose of the present invention, an isocyanate group and a hydrolyzable group are regarded as different groups. The isocyanate group or the hydrolyzable group is a structural unit which is very important to increase the adhesion with various substrates when the substrates are treated with compound A. Here, "adhesion" means a chemical or physical bonding state between compound A and the substrate.

The hydrolyzable group may, for example, be an alkoxy group, a halogen atom (chlorine, bromine or iodine), an acyloxy group, an alkoxy-substituted alkoxy group, an aminoxy group, an amide group, an acid amide group or a ketoximate group, preferably an alkoxy group or a halogen atom. The carbon number of the hydrolyzable group is preferably at most 8, more preferably at most 4. Most preferably, it is a $C_{1-4}$ alkoxy group such as a methoxy group, an ethoxy group, a n-propoxy group or a n-butoxy group.

$Z^1$ to $Z^3$ in compound A are not particularly limited and may be suitably selected depending upon the particular purpose. Further, $Z^1$ to $Z^3$ may be the same or different. However, in view of efficiency in the synthesis, they are preferably the same.

When $Z^1$ to $Z^3$ are different, a hydrolyzable group and an isocyanate group may be coexistent in the molecule, and likewise an isocyanate group and a chlorine atom may be coexistent. Further, different hydrolyzable groups may be coexistent. However, in view of the reactivity of compound A, at least one of $Z^1$ to $Z^3$ is preferably an isocyanate group. It is particularly preferred that all of $Z^1$ to $Z^3$ are isocyanate groups from the viewpoint of the adhesion with a substrate, the safety in the treatment operation, etc.

In the following description, compound A having a structure wherein at least one isocyanate group is present in the molecule of compound A and the isocyanate group is directly bonded to a silicon atom, will be referred to as isocyanate compound A.

In isocyanate compound A, the reactivity of the isocyanate group is very high, and it is considered that the majority of isocyanate groups will be bonded to the surface of the substrate by a chemical reaction when the substrate is treated at a normal temperature. Namely, in the bonded state, the isocyanate group is believed to be modified. For example, the isocyanate group is considered to be reacted with a silanol group of the surface of glass, and it is also considered that a silanol group formed by dissociation of the isocyanate group, will react.

In compound A, each of a to f is 0, 1 or 2, provided $1 \leq a+b \leq 3$, $0 \leq c+d \leq 2$, $1 \leq e+f \leq 3$, and $2 \leq a+b+c+d+e+f \leq 7$. In compound A, in view of the adhesion to a substrate, it is preferred that the number of isocyanate groups and/or hydrolyzable groups directly bonded to one silicon atom is large, it is particularly preferred that the number of isocyanate groups is large. The number of isocyanate groups is preferably such that (the number of isocyanate groups in isocyanate compound A)/(the number of silicon atoms in isocyanate compound A) is at least 1.

Further, n is an integer of 0 or at least 1. There is no particular restriction as to the upper limit for n, and n may be suitably determined depending upon the particular purpose. However if n is too large, the working efficiency during the treatment tends to be poor and practical utility tends to be low. Therefore, n is preferably from 0 to 5, more preferably from 0 to 3 and most preferably 0.

When n is 0, compound A may preferably be a compound of the following formula (A2) or (A3).

$$(R_f^1)(OCN)_2SiOSi(R_f^2)(NCO)_2 \qquad (A2)$$

In the formula (A2), each of $R_f^1$ and $R_f^2$ which are independent of each other, is a polyfluoroorganic group. In the following description, a compound of the formula (A2) will be referred to as compound A2. $R_f^1$ and $R_f^2$ of compound A2 may be the same or different, but preferably the same. As the polyfluoroorganic group, $R_f$ is preferred, and particularly preferred is a perfluoroalkyl group or a group having a perfluoroalkyl moiety. Each of $R_f^1$ and $R_f^2$ is preferably $R_f$ having a perfluoroalkyl moiety represented by $C_aF_{2a+1}(CH_2)_b-$, wherein a is an integer of from 3 to 21, and b is an integer of from 1 to 6, preferably 2, like the one described in the foregoing.

$$(R_f^3)(OCN)_2SiOSi(NCO)_3 \qquad (A3)$$

In the formula (A3), $R_f^3$ is a polyfluoroorganic group. In the following description, a compound of the formula (A3) will be referred to as compound A3. The polyfluoroorganic group is preferably $R_f$ and particularly preferred is a perfluoroalkyl group or a group having a perfluoroalkyl moiety. $R_f^3$ is likewise preferably $R_f$ having a perfluoroalkyl moiety represented by $C_aF_{2a+1}(CH_2)_b-$, wherein a is an integer of from 3 to 21, and b is an integer of from 1 to 6, preferably 2, like the one described in the foregoing.

Compound A in the present invention is a compound having at least two siloxane bonds, and it is believed that during the treatment, a reaction among isocyanate groups or hydrolyzable groups takes place also among molecules of compound A to form siloxane bonds. Accordingly, the film obtained by the treating agent of the present invention has very high cross-linking nature and density, which is believed to contribute to the high mechanical strength and chemical stability of the film.

Further, compound A is a substance having a low surface free energy, and it is considered that free state compound A present in a very small amount in the coating film will move on the very surface layer to reduce the frictional resistance at the surface, whereby the abrasion resistance is excellent.

Now, specific examples of compound A will be shown as (A-1) to (A-151). However, compound A is not limited to such specific examples. In the formulas (A-1) to (A151), Z is an isocyanate group or a hydrolyzable group, R is an organic group, $R_f$ is a polyfluoroalkyl group, Ph is a phenyl group, and n is an integer of 0 or at least 1.

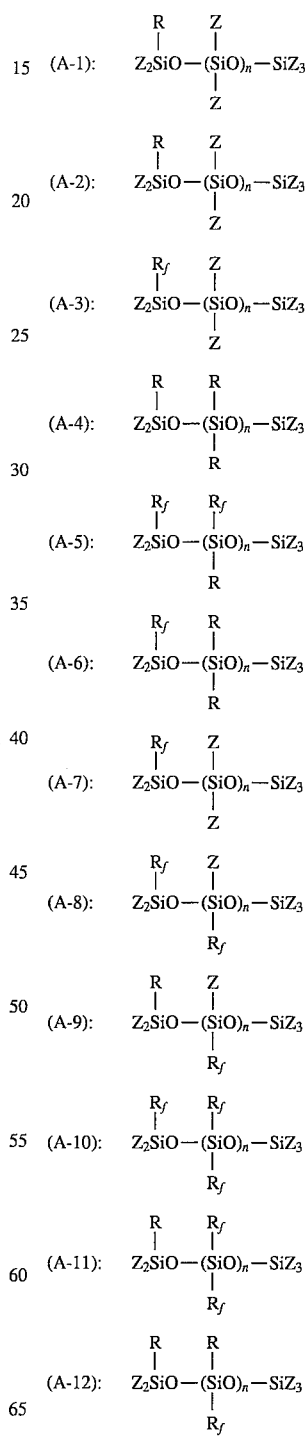

(A-13): $Z_2SiO-(SiO)_n-SiZ_2$ with R, Z, R above and Z below (A-14): $Z_2SiO-(SiO)_n-SiZ_2$ with R, R, R above and Z below (A-15): $Z_2SiO-(SiO)_n-SiZ_2$ with R, R, R above and R below (A-16): $Z_2SiO-(SiO)_n-SiZ_2$ with $R_f$, Z, R above and Z below (A-17): $Z_2SiO-(SiO)_n-SiZ_2$ with $R_f$, $R_f$, R above and Z below (A-18): $Z_2SiO-(SiO)_n-SiZ_2$ with R, $R_f$, R above and Z below (A-19): $Z_2SiO-(SiO)_n-SiZ_2$ with $R_f$, $R_f$, $R_f$ above and R below (A-20): $Z_2SiO-(SiO)_n-SiZ_2$ with R, $R_f$, R above and $R_f$ below (A-21): $Z_2SiO-(SiO)_n-SiZ_2$ with $R_f$, R, $R_f$ above and Z below (A-22): $Z_2SiO-(SiO)_n-SiZ_2$ with R, $R_f$, R above and R below (A-23): $Z_2SiO-(SiO)_n-SiZ_2$ with $R_f$, Z, $R_f$ above and Z below (A-24): $Z_2SiO-(SiO)_n-SiZ_2$ with $R_f$, $R_f$, $R_f$ above and Z below (A-25): $Z_2SiO-(SiO)_n-SiZ$ with $R_f$, $R_f$, $R_f$ above and $R_f$ below (A-26): $Z_2SiO-(SiO)_n-SiZ$ with $R_f$, R, $R_f$ above and Z below (A-27): $Z_2SiO-(SiO)_n-SiZ$ with $R_f$, R, R above and Z below (A-28): $Z_2SiO-(SiO)_n-SiZ$ with R, $R_f$, $R_f$ above and $R_f$ below (A-29): $Z_2SiO-(SiO)_n-SiZ$ with $R_f$, R, R above and $R_f$ below (A-30): $Z_2SiO-(SiO)_n-SiZ$ with $R_f$, R, R above and R below (A-31): $ZSiO-(SiO)_n-SiZ_3$ with R, Z above and R, Z below (A-32): $ZSiO-(SiO)_n-SiZ_3$ with R, R above and R, Z below (A-33): $ZSiO-(SiO)_n-SiZ_3$ with R, Z above and R, Z below (A-34): $ZSiO-(SiO)_n-SiZ_3$ with $R_f$, Z above and R, Z below (A-35): $ZSiO-(SiO)_n-SiZ_3$ with $R_f$, R above and R, Z below (A-36): $ZSiO-(SiO)_n-SiZ_3$ with $R_f$, Z above and $R_f$, Z below (A-37): $ZSiO-(SiO)_n-SiZ_3$ with $R_f$, R above and $R_f$, R below (A-38): $ZSiO-(SiO)_n-SiZ_3$ with $R_f$, $R_f$ above and R, R below (A-39): $ZSiO-(SiO)_n-SiZ_3$ with $R_f$, $R_f$ above and $R_f$, R below (A-40): $ZSiO-(SiO)_n-SiZ_3$ with $R_f$, Z above and $R_f$, Z below -continued (A-41): $\text{ZSiO}-(\text{SiO})_n-\text{SiZ}_3$ with $R_f, R_f$ above and $R_f, Z$ below (A-42): $\text{ZSiO}-(\text{SiO})_n-\text{SiZ}_3$ with $R_f, R_f$ above and $R_f, R_f$ below (A-43): $\text{ZSiO}-(\text{SiO})_n-\text{SiZ}_3$ with $R, R_f$ above and $R, Z$ below (A-44): $\text{ZSiO}-(\text{SiO})_n-\text{SiZ}_3$ with $R, R_f$ above and $R, Z$ below (A-45): $\text{ZSiO}-(\text{SiO})_n-\text{SiZ}_3$ with $R, R_f$ above and $R, R_f$ below (A-46): $\text{ZSiO}-(\text{SiO})_n-\text{SiZ}_3$ with $R_f, R_f$ above and $R, R_f$ below (A-47): $\text{ZSiO}-(\text{SiO})_n-\text{SiZ}_2$ with $R, Z, R$ above and $R, Z$ below (A-48): $\text{ZSiO}-(\text{SiO})_n-\text{SiZ}_2$ with $R, R, R$ above and $R, Z$ below (A-49): $\text{ZSiO}-(\text{SiO})_n-\text{SiZ}_2$ with $R, R, R$ above and $R, R$ below (A-50): $\text{ZSiO}-(\text{SiO})_n-\text{SiZ}_2$ with $R_f, Z, R$ above and $R_f, Z$ below (A-51): $\text{ZSiO}-(\text{SiO})_n-\text{SiZ}_2$ with $R_f, R, R$ above and $R, R$ below (A-52): $\text{ZSiO}-(\text{SiO})_n-\text{SiZ}_2$ with $R_f, R_f, R_f$ above and $R, Z$ below (A-53): $\text{ZSiO}-(\text{SiO})_n-\text{SiZ}_2$ with $R_f, R, R_f$ above and $R_f, Z$ below (A-54): $\text{ZSiO}-(\text{SiO})_n-\text{SiZ}_2$ with $R_f, R, R_f$ above and $R, Z$ below (A-55): $\text{ZSiO}-(\text{SiO})_n-\text{SiZ}_2$ with $R_f, R, R$ above and $R, Z$ below (A-56): $\text{ZSiO}-(\text{SiO})_n-\text{SiZ}_2$ with $R, R, R_f$ above and $R, R$ below (A-57): $\text{ZSiO}-(\text{SiO})_n-\text{SiZ}_2$ with $R_f, R_f, R_f$ above and $R, R_f$ below (A-58): $\text{ZSiO}-(\text{SiO})_n-\text{SiZ}_2$ with $R_f, R, R_f$ above and $R_f, R_f$ below (A-59): $\text{ZSiO}-(\text{SiO})_n-\text{SiZ}_2$ with $R, R, R_f$ above and $R_f, R_f$ below (A-60): $\text{ZSiO}-(\text{SiO})_n-\text{SiZ}_2$ with $R_f, R, R_f$ above and $R_f, R$ below (A-61): $\text{ZSiO}-(\text{SiO})_n-\text{SiZ}_2$ with $R, R, R_f$ above and $R, R_f$ below (A-62): $\text{ZSiO}-(\text{SiO})_n-\text{SiZ}_2$ with $R, R, R_f$ above and $R_f, R$ below (A-63): $\text{ZSiO}-(\text{SiO})_n-\text{SiZ}_2$ with $R, R, R_f$ above and $R, R$ below (A-64): $\text{ZSiO}-(\text{SiO})_n-\text{SiZ}_2$ with $R_f, R, R$ above and $R, R$ below (A-65): $\text{ZSiO}-(\text{SiO})_n-\text{SiZ}_2$ with $R_f, Z, R_f$ above and $R_f, Z$ below (A-66): $\text{ZSiO}-(\text{SiO})_n-\text{SiZ}_2$ with $R_f, R_f, R_f$ above and $R_f, Z$ below (A-67): $\text{ZSiO}-(\text{SiO})_n-\text{SiZ}_2$ with $R_f, R_f, R_f$ above and $R_f, R_f$ below (A-68): $\text{ZSiO}-(\text{SiO})_n-\text{SiZ}_2$ with $R_f, Z, R_f$ above and $R, Z$ below

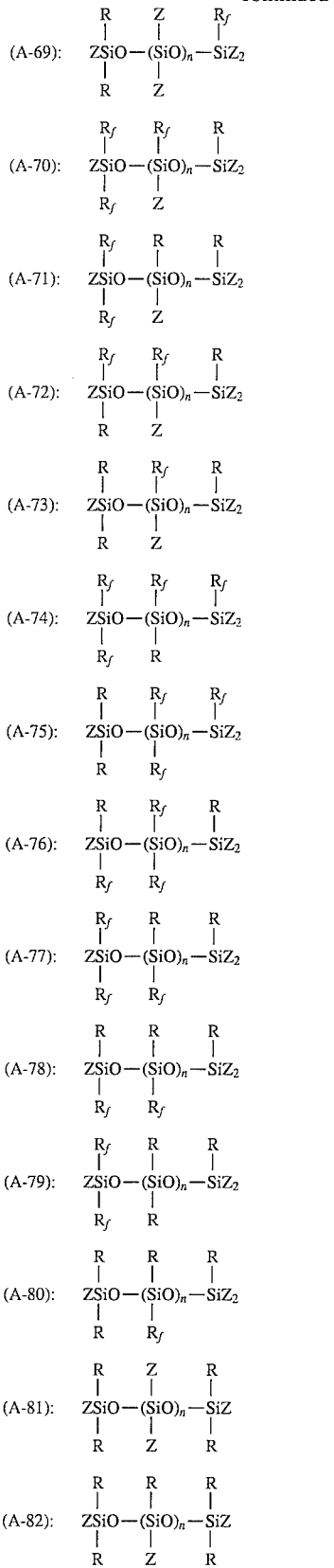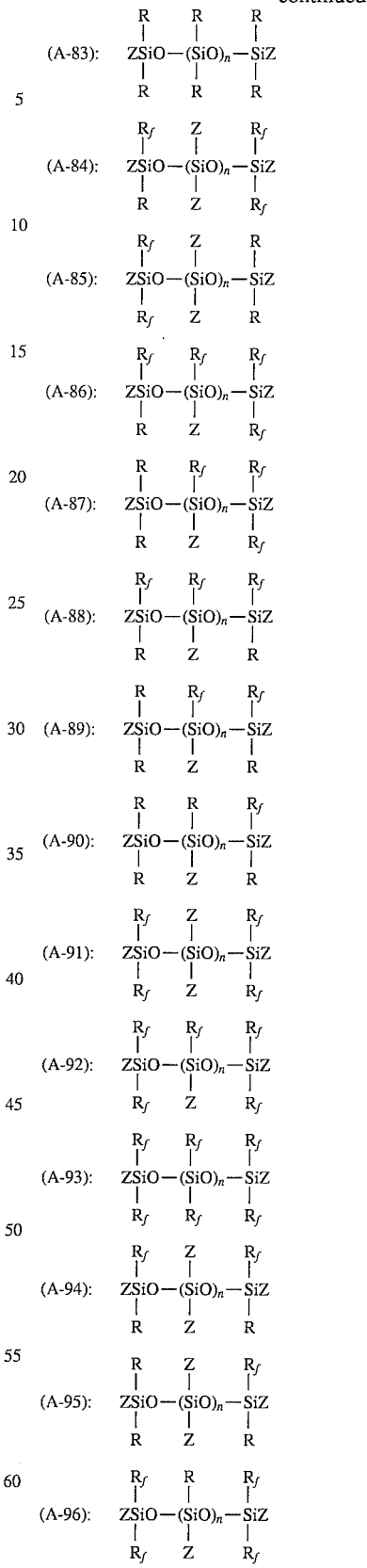

(A-97): $R_f$—$\text{ZSiO}$—$(\text{SiO})_n$—$\text{SiZ}$ with R, R, Z, R, $R_f$, $R_f$ substituents (A-98): $\text{ZSiO}$—$(\text{SiO})_n$—$\text{SiZ}$ with R, R, R, Z, $R_f$, $R_f$ (A-99): $\text{ZSiO}$—$(\text{SiO})_n$—$\text{SiZ}$ with $R_f$, R, $R_f$, R, Z, R (A-100): $\text{ZSiO}$—$(\text{SiO})_n$—$\text{SiZ}$ with R, $R_f$, R, R, Z, R (A-101): $(\text{OCN})_3\text{SiOSi}(\text{NCO})_2$ — $\text{CH}_3$ (A-102): $(\text{OCN})_3\text{SiOSi}(\text{NCO})_2$ — $(\text{CH}_2)_2\text{CF}_3$ (A-103): $(\text{OCN})_3\text{SiOSi}(\text{NCO})_2$ — $\text{C}_8\text{H}_{17}$ (A-104): $(\text{OCN})_3\text{SiOSi}(\text{NCO})_2$ — $(\text{CH}_2)_2\text{C}_4\text{F}_9$ (A-105): $(\text{OCN})_3\text{SiOSi}(\text{NCO})_2$ — $\text{C}_{18}\text{H}_{37}$ (A-106): $(\text{OCN})_3\text{SiOSi}(\text{NCO})_2$ — $(\text{CH}_2)_2\text{C}_8\text{F}_{17}$ (A-107): $(\text{OCN})_3\text{SiOSi}(\text{NCO})_2$ — Ph (A-108): $(\text{OCN})_3\text{SiOSi}(\text{NCO})_2$ — $\text{C}_8\text{F}_{17}\text{CONH}(\text{CH}_2)_3$ (A-109): $(\text{OCN})_3\text{SiOSi}(\text{NCO})_2$ — $\text{C}_8\text{F}_{17}\text{CONHC}_2\text{H}_4\text{NH}(\text{CH}_2)_3$ (A-110): $(\text{OCN})_3\text{SiOSi}(\text{NCO})_2$ — $\text{C}_8\text{F}_{17}\text{C}_2\text{H}_4\text{OCOC}_2\text{H}_4\text{S}(\text{CH}_2)_3$ (A-111): $(\text{OCN})_3\text{SiOSi}(\text{NCO})_2$ — $\text{C}_8\text{F}_{17}\text{C}_2\text{H}_4\text{OCONH}(\text{CH}_2)_3$ (A-112): $(\text{OCN})_3\text{SiOSi}(\text{NCO})_2$ — $(\text{CH}_2)_2\text{C}_8\text{F}_{17}$ (A-113): $(\text{OCN})_2\text{SiOSi}(\text{NCO})_2$ with Cl, $(\text{CH}_2)_2\text{C}_8\text{F}_{17}$ (A-114): $(\text{OCN})_2\text{SiOSi}(\text{NCO})_2$ with $(\text{CH}_2)_2\text{C}_8\text{F}_{17}$, $\text{CH}_3$ (A-115): $(\text{OCN})\text{SiO}$—$\text{Si}(\text{NCO})_2$ with Cl, $(\text{CH}_2)_2\text{C}_8\text{F}_{17}$ (A-116): $(\text{OCN})\text{SiO}$—$\text{Si}(\text{NCO})$ with $(\text{CH}_2)_2\text{C}_8\text{F}_{17}$, $(\text{CH}_2)_2\text{C}_8\text{F}_{17}$, Cl, Cl (A-117): $(\text{OCN})_2\text{SiOSi}(\text{NCO})_2$ with $\text{C}_{18}\text{H}_{37}$, $\text{CH}_3$ (A-118): $(\text{OCN})_2\text{SiOSi}(\text{NCO})_2$ with $(\text{CH}_2)_2\text{C}_8\text{F}_{17}$, $(\text{CH}_2)_2\text{C}_4\text{F}_9$ (A-119): $(\text{OCN})\text{SiOSi}(\text{NCO})_3$ with $(\text{CH}_2)_2\text{C}_8\text{F}_{17}$, $\text{CH}_3$ (A-120): $(\text{OCN})\text{SiOSi}(\text{NCO})_3$ with $\text{C}_8\text{H}_{17}$, $\text{CH}_3$ (A-121): $(\text{OCN})\text{SiOSi}(\text{NCO})_3$ with $(\text{CH}_2)_2\text{C}_8\text{F}_{17}$, $(\text{CH}_2)_2\text{C}_8\text{F}_{17}$ (A-122): $(\text{OCN})\text{SiOSi}(\text{NCO})_3$ with $\text{C}_8\text{H}_{17}$, $\text{C}_8\text{H}_{17}$ (A-123): $(\text{OCN})\text{SiO}$—$\text{Si}(\text{NCO})_2$ with $(\text{CH}_2)_2\text{C}_9\text{F}_{17}$, $(\text{CH}_2)_2\text{C}_9\text{F}_{19}$, $(\text{CH}_2)_2\text{C}_8\text{F}_{17}$ (A-124): $(\text{OCN})\text{SiO}$—$\text{Si}(\text{NCO})_2$ with $\text{C}_2\text{H}_4\text{C}_8\text{F}_{17}$, $\text{CH}_3$, $\text{CH}_3$ (A-125): $(\text{OCN})\text{SiO}$—$\text{Si}(\text{NCO})$ with $\text{C}_8\text{F}_{17}(\text{CH}_2)_2\text{C}_8\text{F}_{17}$, $(\text{CH}_2)_2\text{C}_9\text{F}_{19}$, $(\text{CH}_2)_2\text{C}_8\text{F}_{17}$, $(\text{CH}_2)_2\text{C}_9\text{F}_{19}$ (A-126): $(\text{OCN})\text{SiO}$—$\text{Si}(\text{NCO})$ with $\text{CH}_3$, $\text{CH}_3$, $\text{CH}_3$, $\text{CH}_3$ (A-127): $(\text{OCN})\text{SiO}$—$\text{Si}(\text{NCO})$ with $(\text{CH}_2)_2\text{C}_8\text{F}_{17}$, $\text{CH}_3$, $(\text{CH}_2)_2\text{C}_8\text{F}_{17}$, $\text{CH}_3$ (A-128): $(\text{OCN})\text{SiO}$—$\text{Si}(\text{NCO})$ with $\text{CH}_3$, $\text{C}_8\text{H}_{17}$, $\text{CH}_3$, $\text{C}_8\text{H}_{17}$

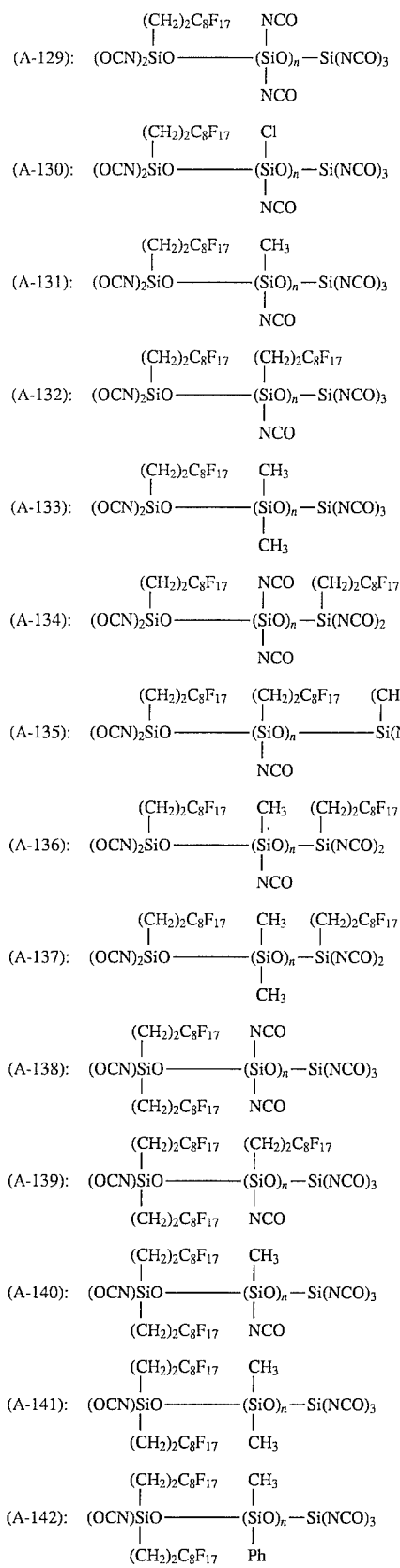

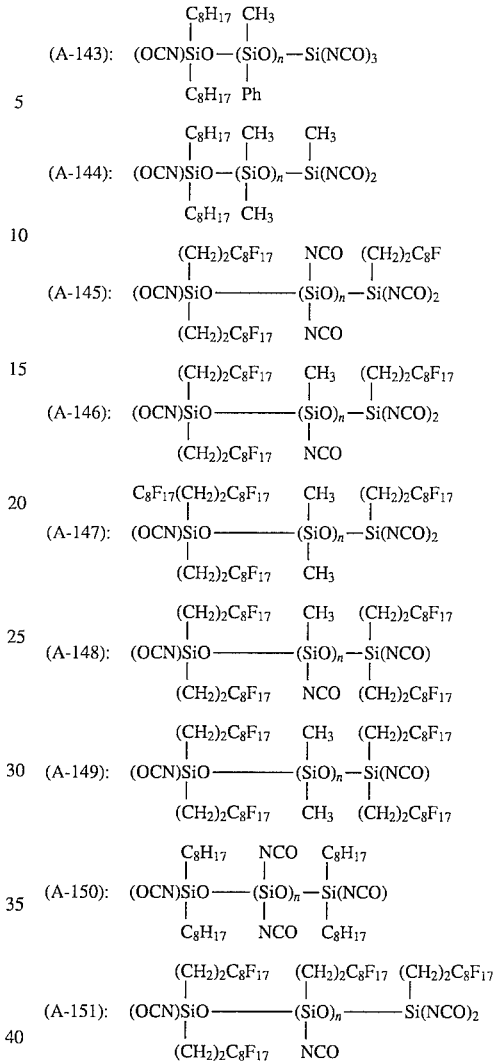

As compound A of the present invention, one or more of the above compounds may be employed.

The surface treating agent of the present invention may be composed solely of compound A. However, it is usually preferred that it contains an organic solvent together with compound A.

The organic solvent is not particularly limited and is preferably an organic solvent which is capable of dissolving or uniformly dispersing compound A of the present invention. Various solvents such as halogenated hydrocarbons, acetic acid esters, aromatic hydrocarbons, ketones or ethers may be employed. Particularly fluorinated hydrocarbons such as 1,1,1,2,2-pentafluoro-3,3-dichloropropane (R225ca) and 1,1,2,2,3-pentafluoro-1,3-dichloropropane (R225cb) are preferred. An organic solvent having a reactive hydrogen atom is undesirable, since such a reactive hydrogen atom will react with the isocyanate group in compound A. Organic solvents may be used alone or in combination as a mixture.

The blend ratio of compound A to the organic solvent is preferably such that the amount of compound A is at a level of from 0.1 to 30 parts by weight per 100 parts by weight of the organic solvent from the viewpoint of the film forming property (operational efficiency), the stability, the thickness of the coating film, the economy, etc.

The surface treating agent of the present invention may contain other compounds and additives depending upon the particular purpose. It is particularly preferred that the surface treating agent of the present invention contains, as such other compounds, other isocyanate silane compounds or silane compounds having hydrolyzable groups, to increase the durability and lasting effects of treatment. It is especially preferred to incorporate compound B of the formula (B):

$$(R^7)_p(R^8)_q(R^9)_r Si(NCO)_{4-p-q-r} \quad (B)$$

wherein each of $R^7$ to $R^9$ which may be the same or different, is a hydrogen atom or a $C_{1-30}$ organic group, and each of p, q and r which are independent of one another, is 0, 1, 2 or 3, provided $0 \leq p+q+r \leq 3$.

However, when compound A is mixed with compound B, etc., the weight % of compound A is preferably at least 50%. If the weight % of compound A is less than 50%, the effects of the present invention tend to be hardly obtainable.

As specific examples of compound B, compounds of the following formulas (B-1) to (B-36) may be mentioned. However, compound B is not limited to such specific examples. In the following chemical formulas, $R_f$ is a polyfluoroalkyl group, and R' is an organic group.

(B-1): $R_fC_2H_4Si(NCO)_3$ (B-2): $R_fC_2H_4Si(NCO)_2$
          |
          R'

(B-3): $(R_fC_2H_4)_2Si(NCO)_2$ (B-4): $(R_fC_2H_4)_3SiNCO$ (B-5): $R_fCONHC_3H_6Si(NCO)_3$ (B-6): $R_fCONHC_3H_6Si(NCO)_2$
          |
          R'

(B-7): $R_fCONHC_2H_4NHC_3H_6Si(NCO)_3$ (B-8): $R_fCOHNC_2H_4NHC_3H_6Si(NCO)_2$
          |
          R'

(B-9): $R_fCON(CH_3)C_2H_4CONH(CH_3)Si(NCO)_3$ (B-10): $R_fCON(CH_3)C_2H_4CONH(CH_3)Si(NCO)_2$
          |
          R'

(B-11): $R_fC_2H_4OCO(CH_2)_2S(CH_2)_3Si(NCO)_3$ (B-12): $R_fC_2H_4OCO(CH_2)_2S(CH_2)_3Si(NCO)_2$
          |
          R'

(B-13): $R_fC_2H_4OCONH(CH_2)_3Si(NCO)_3$ (B-14): $R_fC_2H_4OCONH(CH_2)_3Si(NCO)_2$
          |
          R'

(B-15): $R_fC_2H_4NH(CH_2)_2Si(NCO)_3$ (B-16): $R_fC_2H_4NH(CH_2)_2Si(NCO)_2$
          |
          R'

(B-17): $CF_3C_2F_4O(CFCF_2O)_mCFCONH(CH_2)_3Si(NCO)_3$
              |              |
              CF_3          CF_3

(B-18): $CF_3C_2F_4O(CFCF_2O)_mCFCONH(CH_2)_3Si(NCO)_2$
              |              |              |
              CF_3          CF_3           R'

(B-19): $R'Si(NCO)_3$ (B-20): $R'Si(NCO)_2$
          |
          R'

(B-21): $(R')_3SiNCO$ (B-22): $R'CONHC_3H_6Si(NCO)_3$ (B-23): $R_fCONHC_3H_6Si(NCO)_2$
          |
          R'

(B-24): $R'CONHC_2H_4NHC_3H_6Si(NCO)_3$ (B-25): $R'CONHC_2H_4NHC_3H_6Si(NCO)_2$
          |
          R'

(B-26): $R'CON(CH_3)C_2H_4CONH(CH_3)Si(NCO)_3$ (B-27): $R'CON(CH_3)C_2H_4CONH(CH_3)Si(NCO)_2$
          |
          R'

(B-28): $R'OCO(CH_2)_2S(CH_2)_3Si(NCO)_3$ (B-29): $R'OCO(CH_2)_2S(CH_2)_3Si(NCO)_2$
          |
          R'

(B-30): $R'OCONH(CH_2)_3Si(NCO)_3$ (B-31): $R'OCONH(CH_2)_3Si(NCO)_2$
          |
          R'

(B-32): $R'NH(CH_2)_2Si(NCO)_3$ (B-33): $R'NH(CH_2)_2Si(NCO)_2$
          |
          R'

(B-34): $R'O(CHCH_2O)_mCHCONH(CH_2)_3Si(NCO)_3$
              |           |
              CH_3       CH_3

(B-35): $R'O(CHCH_2O)_mCHCONH(CH_2)_3Si(NCO)_2$
              |           |              |
              CH_3       CH_3           R'

(B-36) $Si(NCO)_2$

Further, the additives may suitably be selected taking the compatibility and the reactivity with various components into consideration. Superfine particles of various metal oxides or various resins may also be incorporated. Further, if coloring is required, dyes or pigments may also be incorporated. Such additives may be incorporated preferably in an amount of from 0.1 to 20 parts by weight per 100 parts by weight of compound A. If the amount of additives is excessive, the antifouling properties, the abrasion resistance, etc. of the surface treating agent of the present invention tend to be low, such being undesirable.

Further, if electrical conductivity is required, a material (such as tin oxide, ITO or zinc oxide) may be incorporated so that a desired resistance can be obtained. The amount of such an additive may suitably be determined depending upon the desired resistance and the material used.

The substrate to be treated with the surface treating agent of the present invention is not particularly limited, and the surface treating agent may be applied to e.g. metals, plastics, ceramics, glass, other inorganic materials or organic materials, or combinations thereof (such as composite materials or laminated materials). Further, the surface of the material may be the surface of the substrate itself as well as the surface of a material different from the substrate itself, such as the surface of a coated film such as coated metal or the surface of glass subjected to surface treatment (such as the surface provided with a sol gel film, a sputtered film, a CVD film or a vapor-deposited film). Further, the shape of the substrate is not particularly limited. For example, it may have an optional shape depending upon the particular purpose, such as the one with a flat surface or the one having a curvature over the entire surface or a part thereof.

Further, prior to applying the treating agent of the present invention, pretreatment may be applied to the substrate depending upon the particular purpose. For example, a pretreatment such as an acid treatment with diluted hydrofluoric acid or hydrochloric acid, alkali treatment with e.g. an aqueous solution of sodium hydroxide or potassium hydroxide, or discharge treatment with e.g. plasma irradiation, may be carried out. Otherwise, the treating agent may be applied direct to the substrate without applying such pretreatment.

The method for applying the treating agent of the present invention to the substrate is not particularly limited. The treating agent of the present invention can be applied by a conventional treating method such as a method of coating it on a substrate surface. As the coating method, various methods may be mentioned including brush coating, casting, rotational coating, dip coating and spraying. Then, it is dried in atmospheric air or nitrogen to form an antifouling coating film.

Each of the above treatments, can be conducted at a normal temperature which is preferably from 20° to 30° C. The drying time is usually from 5 minutes to 5 hours, preferably from 10 minutes to 2 hours. The treating agent of the present invention is an excellent treating agent which is capable of forming a coating film of desired physical properties on the surface of a substrate, simply by coating it at a normal temperature. However, for the purpose of e.g. accelerating the drying, heating may be applied. When heating is applied, the heating temperature and time may be set at levels where the heat resistance of the substrate can be maintained. Further, it is also preferred that the coated substrate is left in a high humidity (e.g. at least 50%) environment for drying.

The thickness of the coating film formed by treating the substrate with the treating agent of the present invention, is suitably controlled by e.g. the concentration of the solid content in the treating agent, the coating conditions, the heating conditions, etc., and it is not particularly limited. In a usual case, the thickness of the coating film may theoretically be at least a single molecular layer to provide antifouling properties, and it is usually preferred to be at most 2 μm from the viewpoint of economical effects.

Further, the coating film obtainable by the treating agent of the present invention has a low refractive index. By virtue of the low refractive index, low reflectance can also be imparted. When not only antifouling properties but also low reflectance is imparted to the substrate, it is preferred to control the thickness of the coating film to a level where an optical interference will result.

The treating agent of the present invention has a merit in that the desired properties can be obtained by treatment at a normal temperature. It requires no special pretreatment or post-treatment, whereby treatment can be easily accomplished. Accordingly, it is suitable for treatment of not only a new substrate but also a substrate which has already been used for some purpose. Further, the treating agent of the present invention may be used for the purpose of repairing, when the performance of the coating film has deteriorated for some reason. Further, it may be applied locally. Namely, the treating agent of the present invention is an excellent treating agent which can be applied for a wide range of applications.

Further, the following film structures have been found effective as means for further remarkably improving the effects of the surface treating agent of the present invention.

The first one is a substrate having at least two treated surface layers, wherein the first layer constituting the outermost layer among the treated surface layers is a layer formed by treatment with the surface treating agent containing compound A, and the second layer constituting an underlayer in contact with the outermost layer is a layer formed by treatment with a treating agent containing a compound (C) capable of forming a thin film of a heat-resistant polymer.

Another one is a substrate having at least two treated surface layers, wherein the first layer constituting the outermost layer among the treated surface layers is a layer formed by treatment with the surface treating agent containing compound A, and the second layer constituting an underlayer in contact with the outermost layer is a layer formed by treating the substrate surface with a treating agent containing a compound (C) capable of forming a thin film of a heat-resistant polymer and fine particles of a polymer, to form a thin film and heating the thin film to thermally decompose the fine particles of a polymer.

Here, the treating agent containing a compound (C) capable of forming a thin film of a heat-resistant polymer (hereinafter referred to simply as compound C), and the second layer formed by treatment therewith, will be described.

In the present invention, compound C is used as a material for forming the second layer. The second layer will remarkably improve the durability of the first layer as its upper layer, and it is also effective for improving the adhesion with the substrate. This second layer is usually formed on the substrate surface. The substrate surface may already be coated with a vapor-deposited film, a sputtered film or various films formed by a wet method.

As the above various films, an antistatic film, a transparent conductive film, an electromagnetic wave-shielding film, an ultraviolet-absorbing film, a heat ray-absorbing film and a heat ray-reflecting film may, for example, be mentioned. These films may be used in combination. The materials for such various films are not particularly limited, and films containing oxides of metals such as Sr, Zr, Ti, Zn, Al, Sn, Sb, Pb and Ta, may be mentioned.

Compound C to be used for forming the second layer is not particularly limited and may be suitably selected depending upon the particular purpose. Polymer compounds made of various commercially available materials, may be employed. Compound C may be a heat-resistant polymer itself, or may be a compound which is capable of being converted to a heat-resistant polymer e.g. by polymerization at the time of the treatment.

Compound C is capable of forming a thin film on the surface of e.g. a substrate at the time of treatment. For example, compound C dissolved or dispersed in the treating agent is required to form a thin film of a heat-resistant polymer upon removal of e.g. the solvent at the time of treatment. Specifically, a solution or dispersion of a heat-resistant polymer itself or a compound capable of forming a heat-resistant polymer by cross-linking, may be used. Further, a solution or dispersion of a compound capable of forming a heat-resistant polymer by hydrolysis, such as a tetraalkoxysilane, or its partial hydrolyzate, may also be used.

Compound C may, for example, be a polyethylene resin, a polypropylene resin, a polystyrene resin, a polyacrylate resin, a polymethyl methacrylate resin, a polyvinyl chloride resin, a polyvinyl alcohol resin, a polycarbonate resin, a polyacetal resin, a polyester resin, a polyamide resin, a polyimide resin, a fluorine resin, a phenol resin, an epoxy resin or a silicone resin. Preferred as compound C is a reactive silane compound or a partial hydrolyzate thereof.

The reactive silane compound is used as a general term covering both of the following "hydrolyzable silane compound" and "isocyanate silane compound". The "hydrolyzable silane compound" is a compound wherein at least one hydrolyzable group is bonded to a silicon atom. The "isocyanate silane compound" is a compound wherein at least one isocyanate group is bonded to a silicon atom.

An "isocyanate group" may be regarded as a kind of "hydrolyzable groups". However, as mentioned above, for the purpose of the present invention, an isocyanate group bonded to a silicon atom is distinguished from a hydrolyzable group.

The surface treated with an "isocyanate silane compound" is a surface to which the "isocyanate silane compound" is chemically or physically bonded. An isocyanate group is reactive. Accordingly, the "isocyanate silane compound" is believed to be bonded to the surface of the treated layer mainly by a chemical reaction. Namely, in the bonded state, the isocyanate group is believed to have been modified. For example, it is considered that the isocyanate group is reacted with a silanol group on the surface of glass, and a silanol group formed by dissociation of an isocyanate group, will react.

The "isocyanate silane compound" is considered to provide such properties as the abrasion resistance, the chemical resistance and the weather resistance by virtue of such a reactivity of the isocyanate group and the siloxane structure formed by the reaction among molecules of the isocyanate silane compound.

The surface treated with a "hydrolyzable silane compound" is the surface to which the "hydrolyzable silane compound" is chemically or physically bonded. The hydrolyzable group is reactive. Accordingly, the "hydrolyzable silane compound" is considered to be bonded to the surface of the treated layer mainly by a chemical reaction. Namely, in the bonded state, the hydrolyzable group is believed to have been changed.

The hydrolyzable group in this "hydrolyzable silane compound" is a group directly bonded to a silicon atom. The hydrolyzable group may, for example, be a halogen atom, an alkoxy group, an acyloxy group, an alkoxy-substituted alkoxy group, an aminoxy group, an amide group or a ketoximate group. Preferred is a hydrolyzable group bonded via an oxygen atom to a silicon atom, such as an alkoxy group, an alkoxy-substituted alkoxy group or an acyloxy group. Such a hydrolyzable group is preferably the one having at most 8 carbon atoms, more preferably the one having at most 4 carbon atoms. More preferably, it is a $C_{1-4}$ alkoxy group.

The "hydrolyzable silane compound" is considered to provide such properties as abrasion resistance, chemical resistance and weather resistance by virtue of the reactivity of the hydrolyzable group or the siloxane structure formed by the reaction among molecules of the hydrolyzable silane compound.

The "hydrolyzable silane compound" may be used as it is or may be used in the form of a partially hydrolyzed product obtained by its hydrolysis. The partially hydrolyzed product of the "hydrolyzable silane compound" is a compound having a silanol group formed by partially hydrolyzing such a hydrolyzable silane compound in water or in an acidic aqueous solution, or a compound having two or more molecules condensed by the reaction of the silanol groups. As the acid, hydrochloric acid, nitric acid, acetic acid, sulfuric acid, phosphoric acid or sulfonic acid may, for example, be used.

The above reactive silane compounds may be used in combination as a mixture of two or more of them. However, it is better to avoid combined use of the "isocyanate silane compound" and the "hydrolyzable silane compound" because the isocyanate group and the hydrolyzable group are likely to react, whereby the effective life of the treating agent may be shortened.

A preferred reactive silane compound is a compound having one or two hydrolyzable groups and/or isocyanate groups directly bonded to a silicon atom. More preferred as such a compound are a compound of the following formula (C1) which may also be referred to as compound C1 and a compound of the following formula (C2) which may also be referred to as compound C2:

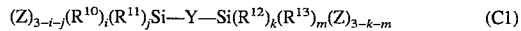

$$(Z)_{3-i-j}(R^{10})_i(R^{11})_j Si—Y—Si(R^{12})_k(R^{13})_m(Z)_{3-k-m} \qquad (C1)$$

wherein each of $R^{10}$, $R^{11}$, $R^{12}$ and $R^{13}$ which are independent of one another, is a hydrogen atom, a hydroxyl group, an amino group or a $C_{1-30}$ organic group;

Y is a bivalent organic group;

Z is an isocyanate group and/or a hydrolyzable group;

each of i and j which are independent of each other, is an integer of 0, 1 or 2, provided $0 \leq i+j \leq 2$; and each of k and m which are independent of each other, is an integer of 0, 1 or 2, provided $0 \leq k+m \leq 2$;

$$(R^{14})_e(R^{15})_g(R^{16})_h Si(Z)_{4-e-g-h} \qquad (C2)$$

wherein each of $R^{14}$ $R^{15}$ and $R^{16}$ which are independent of one another, is a hydrogen atom or a $C_{1-30}$ organic group, provided that at least one of them is the organic group;

Z is an isocyanate group and/or a hydrolyzable group; and each of e, g and h which are independent of one another, is an integer of 0, 1 or 2, provided $0 \leq e+g+h \leq 3$.

The reactive silane compound used to form the second layer will firmly bond to the first layer and the underlayer (such as the substrate) by virtue of the reactivity of the isocyanate group or the hydrolyzable group. The siloxane structure resulted from the isocyanate group or the hydrolyzable group will contribute to improvement of the abrasion resistance. Accordingly, the larger the number, per a silicon atom, of isocyanate groups or hydrolyzable groups directly bonded to a silicon atom, the better.

In a case where the reactive silane compound is compound C1 or compound C2, the organic group is preferably an organic group which is not an organic group having fluorine atoms, particularly a hydrocarbon group. Most preferably, the organic group is a lower alkyl group or an alkylene group having at most 6 carbon atoms.

When compound A to be used for the first layer has an organic group having fluorine atoms, the organic group of compound C1 or C2 may be the one having a lower hydrophobic nature relative to such an organic group, and it may sometimes be a long chain hydrocarbon group.

Especially when the adhesion to the first layer and the underlayer (such as the substrate) is taken into consideration, the larger the number of isocyanate groups or hydrolyzable groups bonded to a silicon atom, the better. With respect to compound C1, a compound of the formula (C1) wherein i=j=k=m=0 is preferred, and with respect to compound C2, a compound of the formula (C2) wherein e=g=h=0 is preferred.

Specifically, tetraisocyanate silane or a tetraalkoxysilane may, for example, be mentioned.

Specific examples of compound C1 includes compounds of the following formulas (C-1) to (C-87). Specific examples of compound C2 include compounds of the formulas (B-1) to (B-36) as previously exemplified as compound B. Further, compounds corresponding to the exemplified compounds wherein the isocyanate groups are substituted by hydrolyzable groups, may also be mentioned. In the following formulas, p is an integer, preferably an integer of from 2 to 8.

(C-1): 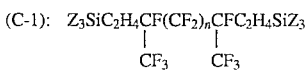

(C-2): 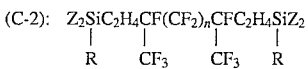

(C-3): 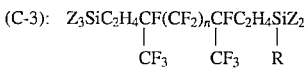

(C-4): 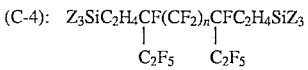

(C-5): 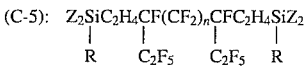

(C-6): 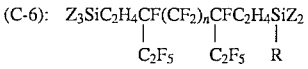

(C-7): 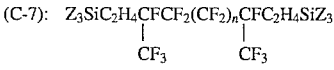

(C-8): 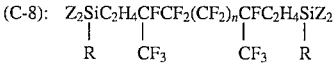

(C-9): 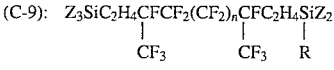

(C-10): 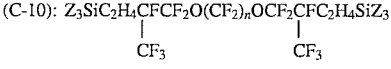

(C-11): 

(C-12): 

(C-13): 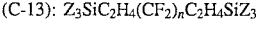

(C-14): 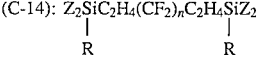

(C-15): 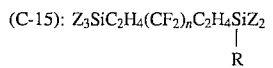

(C-16): 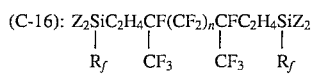

(C-17): 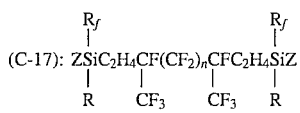

(C-18): 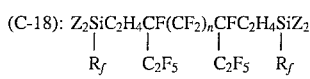

(C-19): 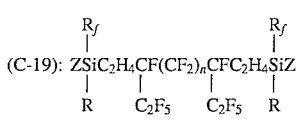

(C-20): 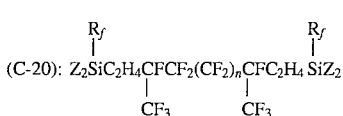

(C-21): 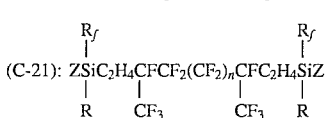

(C-22): 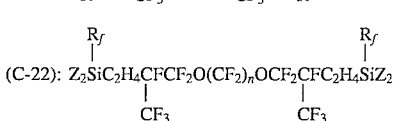

(C-23): 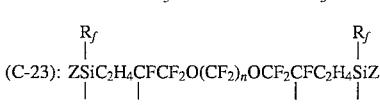

(C-24): 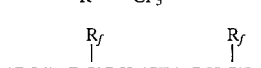

(C-25): 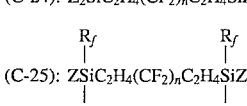

(C-26): 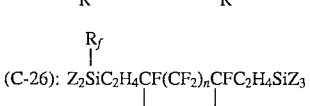

(C-27): 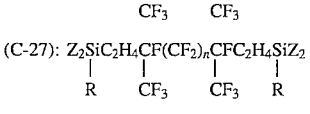

(C-28): 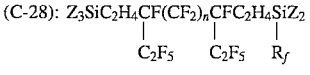

(C-29): 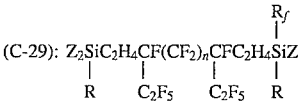

(C-30): 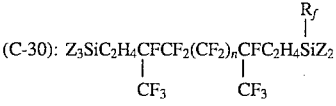

(C-31): $Z_2SiC_2H_4CFCF_2(CF_2)_nCFC_2H_4SiZ$ with $R_f$ on second Si, $R$ on first C, $CF_3$ on second C, $CF_3$ on third C, $R$ on fourth C (C-32): $Z_3SiC_2H_4CFCF_2O(CF_2)_nOCF_2CFC_2H_4SiZ_2$ with $R_f$ on second Si, $CF_3$ on first C, $CF_3$ on second C (C-33): $Z_2SiC_2H_4CFCF_2O(CF_2)_nOCF_2CFC_2H_4SiZ$ with $R_f$ on second Si, $R$ on first C, $CF_3$ on second C, $CF_3$ on third C, $R$ on fourth C (C-34): $Z_3SiC_2H_4(CF_2)_nC_2H_4SiZ_2$ with $R_f$ on second Si (C-35): $Z_2SiC_2H_4(CF_2)_nC_2H_4SiZ$ with $R_f$ on second Si, $R$ on first Si, $R$ on second Si (C-36): $ZSiC_2H_4CF(CF_2)_nCFC_2H_4SiZ_3$ with $R_f$ on first Si, $R$ on first Si, $CF_3$, $CF_3$ (C-37): $Z_2SiC_2H_4CF(CF_2)_nCFC_2H_4SiZ_2$ with $R_f$ on second Si, $R$ on first C, $CF_3$, $CF_3$ (C-38): $Z_3SiC_2H_4CF(CF_2)_nCFC_2H_4SiZ$ with $R$ on second Si, $C_2F_5$, $C_2F_5$, $R_f$ (C-39): $Z_2SiC_2H_4CF(CF_2)_nCFC_2H_4SiZ_2$ with $R_f$ on second Si, $R$ on first C, $C_2F_5$, $C_2F_5$ (C-40): $Z_3SiC_2H_4CFCF_2(CF_2)_nCFC_2H_4SiZ$ with $R_f$ on second Si, $CF_3$, $CF_3$, $R$ (C-41): $Z_2SiC_2H_4CFCF_2(CF_2)_nCFC_2H_4SiZ_2$ with $R_f$ on second Si, $R$ on first C, $CF_3$, $CF_3$ (C-42): $Z_3SiC_2H_4CFCF_2O(CF_2)_nOCF_2CFC_2H_4SiZ$ with $R_f$ on second Si, $CF_3$, $CF_3$, $R$ (C-43): $Z_2SiC_2H_4CFCF_2O(CF_2)_nOCF_2CFC_2H_4SiZ_2$ with $R_f$ on second Si, $R$ on first C, $CF_3$, $CF_3$ (C-44): $Z_3SiC_2H_4(CF_2)_nC_2H_4SiZ$ with $R_f$ on second Si, $R$ on second Si (C-45): $Z_2SiC_2H_4(CF_2)_nC_2H_4SiZ_2$ with $R_f$ on second Si, $R$ on first Si (C-46): $Z_2SiC_2H_4SiZ_2$ with $R_f$, $R_f$ (C-47): $Z_2SiC_2H_4SiZ_3$ with $R_f$ (C-48): $ZSiC_2H_4SiZ_3$ with $R$, $R_f$ (C-49): $ZSiC_2H_4SiZ_2$ with $R$, $R$, $R_f$ (C-50): $Z_2SiC_2H_4SiZ_2$ with $R$, $R_f$ (C-51): $ZSiC_2H_4SiZ$ with $R_f$, $R_f$, $R$, $R$ (C-52): $ZSiC_2H_4SiZ_2$ with $R_f$, $R_f$, $R$ (C-53): $Z_2SiC_2H_4OC_2H_4SiZ_2$ with $R_f$, $R_f$ (C-54): $Z_2SiC_2H_4OC_2H_4SiZ_3$ with $R_f$ (C-55): $ZSiC_2H_4OC_2H_4SiZ_3$ with $R$, $R_f$ (C-56): $ZSiC_2H_4OC_2H_4SiZ_2$ with $R$, $R$, $R_f$ (C-57): $Z_2SiC_2H_4OC_2H_4SiZ_2$ with $R$, $R_f$ (C-58): $ZSiC_2H_4OC_2H_4SiZ$ with $R_f$, $R_f$, $R$, $R$ (C-59): $ZSiC_2H_4OC_2H_4SiZ_2$ with $R_f$, $R_f$, $R$ (C-60): $Z_2SiC_2H_4SC_2H_4SiZ_2$ with $R_f$, $R_f$ (C-61): $Z_2SiC_2H_4SC_2H_4SiZ_3$ with $R_f$ -continued (C-62): $ZSiC_2H_4SC_2H_4SiZ_3$ with R above, $R_f$ below (C-63): $ZSiC_2H_4SC_2H_4SiZ_2$ with R, R above, $R_f$ below (C-64): $Z_2SiC_2H_4SC_2H_4SiZ_2$ with R above, $R_f$ below (C-65): $ZSiC_2H_4SC_2H_4SiZ$ with $R_f$, $R_f$ above, $R_f$, R below (C-66): $ZSiC_2H_4SC_2H_4SiZ_2$ with $R_f$, $R_f$ above, R below (C-67): $Z_2SiC_2H_4OC_2H_4OC_2H_4SiZ_2$ with $R_f$, $R_f$ below (C-68): $Z_2SiC_2H_4OC_2H_4OC_2H_4SiZ_3$ with $R_f$ below (C-69): $ZSiC_2H_4OC_2H_4OC_2H_4SiZ_3$ with R above, $R_f$ below (C-70): $ZSiC_2H_4OC_2H_4OC_2H_4SiZ_2$ with R, R above, $R_f$ below (C-71): $Z_2SiC_2H_4OC_2H_4OC_2H_4SiZ_2$ with R above, $R_f$ below (C-72): $ZSiC_2H_4OC_2H_4OC_2H_4SiZ$ with $R_f$, $R_f$ above, R, R below (C-73): $ZSiC_2H_4OC_2H_4OC_2H_4SiZ_2$ with $R_f$, $R_f$ above, R below (C-74): $Z_2SiC_2H_4SC_2H_4SC_2H_4SiZ_2$ with $R_f$, $R_f$ below (C-75): $Z_2SiC_2H_4SC_2H_4SC_2H_4SiZ_3$ with $R_f$ below (C-76): $ZSiC_2H_4SC_2H_4SC_2H_4SiZ_3$ with R above, $R_f$ below (C-77): $ZSiC_2H_4SC_2H_4SC_2H_4SiZ_2$ with R, R above, $R_f$ below (C-78): $Z_2SiC_2H_4SC_2H_4SC_2H_4SiZ_2$ with R above, $R_f$ below (C-79): $ZSiC_2H_4SC_2H_4SC_2H_4SiZ$ with $R_f$, $R_f$ above, R, R below (C-80): $ZSiC_2H_4SC_2H_4SC_2H_4SiZ_2$ with $R_f$, $R_f$ above, R below (C-81): $Z_3Si(CH_2)_nSiZ_3$ (C-82): $Z_3Si(CH_2)_nSiZ_2$ with R' below (C-83): $Z_2Si(CH_2)_nSiZ_2$ with R', R' below (C-84): $Z_3Si(C_2H_4O)_nC_2H_4SiZ_3$ (C-85): $Z_2Si(C_2H_4O)_nC_2H_4SiZ_3$ with R' below (C-86): $Z_3Si(C_2H_4S)_nC_2H_4SiZ_3$ (C-87): $Z_2Si(C_2H_4S)_nC_2H_4SiZ_3$ with R' below As the treating agent for forming the second layer of the present invention, it is preferred to employ a solution or dispersion containing a reactive silane compound as an essential component. To such a treating agent, other additives may be incorporated in addition to the solvent or the dispersant.

To the treating agent containing the reactive silane compound, other compounds or additives may be added as the case requires. The additives, etc. may be selected taking into consideration the reactivity and compatibility with various components. For example, fine particles of various metal oxides such as silica, alumina, zirconia and titania, or various resins may be incorporated. If coloring is required, a dye or a pigment may be incorporated. The amount of additives may be at a level of from 0.01 to 20 wt %, based on the total weight of other components. Incorporation of an excessive amount is undesirable since the abrasion resistance tends to thereby deteriorate.

Further, if electrical conductivity is required, a material whereby a desired resistance can be obtained (such as tin oxide, ITO or zinc oxide) may be added. The amount of such an additive may be determined depending upon the desired level of resistance and the material.

The above composition may be directly coated by e.g. rubbing. Otherwise, it may be dissolved, dispersed or diluted with an organic solvent for use in the form of a solution.

The total amount of various components contained in the solution of such an organic solvent is determined taking into consideration the moldability (working efficiency) of the coating film, the stability, the thickness of the coating film and economy, and it is preferred to prepare the solution so that the total amount of various components will be from 0.1 to 30 wt %.

As the organic solvent, various organic solvents such as acetic acid esters, aromatic hydrocarbons, halogenated hydrocarbons, ketones, ethers or alcohols, may be employed. However, when the reactive silane compound has an isocyanate group, the one having a reactive functional group (such as a hydroxyl group) is undesirable. Accordingly, alcohols are not suitable for an isocyanate silane compound, but there is no particular restriction as to the hydrolyzable silane compound. The diluting solvent is not limited to one type, and a solvent mixture of two or more different types may also be used.

Further, in the present invention, the second layer may be formed also with a treating agent containing compound C and fine particles of a polymer.

Here, the fine particles of a polymer may, for example, be made of a polyethylene resin, a polypropylene resin, a polystyrene resin, a polyacrylate resin, a polymethyl methacrylate resin, a polyvinyl chloride resin, a polyvinyl alcohol resin, a polycarbonate resin, a polyacetal resin, a polyester resin, a polyamide resin, a polyimide resin, a fluorine resin, a phenol resin, an epoxy resin or a silicone resin. The material for the fine particles of a polymer may be one member selected from such exemplified compounds, or it may be a mixture of two or more different types.

The average particle size of the fine particles of a polymer is not particularly limited, but it is preferably within a range of from 1 to 1000 nm from the viewpoint of the film strength. Especially when transparency is important, the average particle size is preferably at most 500 nm, more preferably at most 200 nm, to avoid scattering of light rays. The shape of the particles is not particularly limited, but it is usually spherical. The material for the particles is preferably a thermoplastic resin such as a polystyrene resin or a polymethyl methacrylate resin among those mentioned above.

The proportion of the fine particles of a polymer in the total amount of the fine particles of a polymer and compound C is not particularly limited, but it is preferably at most 80 wt %, since if the amount of the fine particles of a polymer is too much, the mechanical strength of the coating film formed after the thermal decomposition tends to be low. On the other hand, if it is too small, the effects of incorporation of the fine particles of a polymer can hardly be obtained. Therefore, the amount is preferably at least 5 wt %, more preferably from 5 to 50 wt %.

The heat-resistant polymer formed by compound C is required to be a material having a heat decomposition temperature higher than the heat decomposition temperature of the fine particles of a polymer. Particularly preferred is a material which undergoes no chemical or physical change at the time of the heat decomposition of the fine particles of a polymer. Such a heat-resistant polymer preferably has a heat decomposition temperature higher by at least 50° C. than the heat decomposition temperature of the fine particles of a polymer.

Compound C for forming the second layer is used preferably as diluted together with the fine particles of a polymer and a binder with a solvent, from the viewpoint of the operation efficiency. The solvent to be used for this purpose may be the above-mentioned organic solvent.

For the surface treatment of a substrate, no special pretreatment is required. However, depending upon the particular purpose, pretreatment may be applied. For example, acid treatment with diluted hydrofluoric acid or hydrochloric acid, alkali treatment with an aqueous solution of sodium hydroxide, or discharge treatment with e.g. plasma irradiation may be applied.

Formation of the second layer is not particularly limited, but it is common to employ a method wherein a liquid formulation composed of an organic solvent containing compound C is coated on the surface by a conventional treating method (such as brush coating, casting, rotational coating, dip coating, spray coating, various printing method such as a flexo printing method or a screen printing method) and then dried in atmospheric air or nitrogen.

The drying can adequately be conducted at room temperature. When heat drying is applied, the temperature and the time may be set taking the heat resistance of the substrate into consideration. When fine particles of a polymer are used for the treating agent for forming the second layer, by such heat treatment, the fine particles of a polymer undergoes heat decomposition to form a roughened surface. Accordingly, the heating temperature may be determined depending upon the heat resistance of the substrate and the spherical polymer compound. It is common to carry out the treatment within a temperature range of from 100° to 800°.

The thermal decomposition of the fine particles of a polymer by heat treatment may not necessarily be complete, and adequate effects of the present invention can be obtained even when the fine particles of a polymer partially remain e.g. at the interior of the thin film of the heat-resistant polymer.

The thickness of the second layer is not particularly limited and may be very thin. The thickness is preferably at most 2 μm. The lower limit is a single molecular layer thickness. The thickness being too much is undesirable from the viewpoint of the economy and the quality of appearance.

The substrate to be used in the present invention is preferably a substrate made of a transparent material such as glass or plastics. Further, it is particularly preferred that the substrate is useful for articles of transportation equipments or articles for building or building decorations.

The articles for transportation equipments include exterior parts such as outer panels, window glasses, mirror or display surface materials, and interior parts such as instrument panels, in transportation equipments such as electric cars, automobiles, ships or aircrafts, as well as parts and constituting elements used or to be used for other transportation equipments. For example, bodies, window glasses and pantagraphs of electric cars, bodies, front glasses, side glasses, rear glasses, mirrors or bumpers of automobiles, buses or trucks, bodies and window glasses of ships, and bodies and window glasses of aircrafts, may be mentioned.

Such an article may be composed solely of the surface-treated substrate or may have the surface-treated substrate incorporated therein. For example, the former may be a window glass for an automobile, and the latter may be a back mirror for an automobile in which a glass mirror is incorporated.

With such substrates or articles, water drops on the surface will be repelled by the water repellency. Especially, during driving, due to the interaction with the receiving wind pressure, water drops rapidly move on the surface and will not remain as water drops, whereby any adverse effect which may otherwise be induced by moisture, can be eliminated. Especially in the application to a see-through portion such as a window glass, it becomes easy to secure a viewing field due to dissipation of water drops, thus leading to improvement of the safety of a vehicle. Further, in an environment where water drops usually freeze, no freezing takes place, or even if freezing takes place, the frozen drops can readily be defrosted. Further, there will be no substantial deposition of water drops, whereby the number of periodical cleaning operations can be reduced. Besides, the cleaning operation is very easy, such being advantageous also for the protection of good appearance.

Further, the articles for buildings or building decorations may be articles to be attached to buildings or articles already attached to buildings, or articles for buildings which are not attached to buildings but which are used for the buildings, or articles for buildings such as furnitures or equipments.

For example, they include window glasses, glass plates for roofs, various roofs including glass roofs, glass plates for doors or doors having such glass plates installed, glass plates for partitions, glass plates for green houses, or green houses having such glass plates, window materials or roof materials using transparent plastic plates, wall materials made of ceramics, cement, metals or other materials, mirrors, furnitures having such mirrors, and glass for display shelves or showcases.

Such an article may be made of the surface treated substrate alone or may be the one having the surface treated substrate incorporated therein. For example, the former may be a window glass plate, and the latter may be a furniture in which a glass mirror is incorporated.

With such a surface treated substrate, water drops which are brought in contact with the surface are repelled due to the water repellency and scarcely attach to the surface, or if attached, the amount is small and the attached water drops can easily be removed. Further, even in an environment where water drops usually freeze, no freezing takes place, or even if freezing takes place, the frozen drops can readily be defrosted. Further, there will be no substantial deposition of water drops, whereby the number of periodical cleaning operations can be reduced, and each cleaning operation will be very easy, and such being advantageous also from the viewpoint of the protection of good appearance.

Now, the present invention will be described in further detail with reference to Examples. However, it should be understood that the present invention is by no means restricted to such specific Examples.

In the following Examples, the evaluation methods for antifouling properties and antifouling durability were as follows.

Evaluation method for antifouling properties
  a) The contact angle of water was measured.
  b) The contact angle of hexadecane was measured.
  c) The finger-print removal properties were evaluated by the following method:
    Finger prints were put on the treated surface and wiped with a cotton cloth for 20 reciprocal strokes, whereupon the appearance was inspected and evaluated by the following standards:
    A: Oil stains completely and cleanly wiped off.
    B: Oil stains slightly remain.
    C: Oil stains substantially remain.
  d) The water drop remaining degree was evaluated by the following method.
    From a nozzle held in a distance of 20 cm from a vertically held plate sample, water was sprayed over the entire surface of the sample for about one hour, whereupon water drops remaining on the surface were visually observed and evaluated in accordance with the following evaluation standards:
    A: No water remains on the sample surface.
    B: Water slightly remains on the sample surface.
    C: Water drops remain in a substantial amount on the sample surface.
    D: Water spread wettingly on the sample surface.

Evaluation method for the antifouling durability
  A sample was immersed in boiling water for 3 hours, whereupon c) the finger print removal properties and d) the water drop remaining degree were evaluated.

EXAMPLE 1

Into a flask equipped with a stirrer and a thermometer, 100 g of $C_8F_{17}C_2H_4Si(NCO)_3$ and 900 g of dry ethyl acetate were introduced, and the atmosphere in the flask was flushed with dry nitrogen gas. Then, the mixture was thoroughly stirred at 25° C. for 30 minutes.

To this solution, 2.98 g of distilled water was gradually dropwise added over a period of 3 hours. This solution was stirred for 3 days at 25° C., whereupon ethyl acetate was removed by distillation. The remained powder was washed with ethyl acetate and then thoroughly dried to obtain a reaction product. A mass spectrometric analysis was carried out with respect to the obtained reaction product. The mass spectrometric analysis was carried out by means of SX-102A apparatus manufactured by Nippon Denshi K.K., by employing a direct feeding method as a sample feeding method and a CI+ method (reagent gas:NO) as an ionization method, under such a condition that the temperature rise was from 50° to 260° C. (32° C./min). As a result of the analysis, a peak at 1164 (molecular weight of the reaction product 1134+molecular weight of NO 30) was confirmed as shown in FIG. 1. Further, the infrared spectrum of the obtained reaction product was measured, whereby the peak of NCO was confirmed at 2290 cm$^{-1}$ as shown in FIG. 2. From these results, the reaction product was ascertained to be

$(C_8F_{17}C_2H_4)(OCN)_2SiOSi(C_8F_{17}C_2H_4)(NCO)_2$.

Into a flask equipped with a stirrer and a thermometer, 2.0 g of a compound (a-1) having the following structure and 98.0 g of dichloropentafluoropropane were introduced. While maintaining the temperature of this solution at 25° C., stirring was continued for one day to obtain treating agent 1.

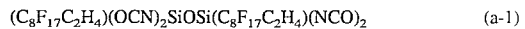

$(C_8F_{17}C_2H_4)(OCN)_2SiOSi(C_8F_{17}C_2H_4)(NCO)_2$ (a-1)

1 cc of treating agent 1 was dropped on a glass plate (10 cm×10 cm×2 mm in thickness) which was preliminarily cleaned, and spread by a JK wiper (product manufactured by Jujo Kimberly K.K.) in a manner similar to waxing an automobile, and the glass plate was left to stand for one day to obtain a sample glass. The antifouling properties and the antifouling durability of the sample glass thus obtained, were evaluated, and the results are shown in Table 1.

Comparative Example 1

The glass plate of Example 1 was evaluated in the same manner without applying any treatment. The results are shown in Table 1.

TABLE 1

| | | Antifouling properties | | | | Antifouling durability | |
|---|---|---|---|---|---|---|---|
| | Appearance | Contact angle Hexadecane | Contact angle Water | Finger print removal properties | Water drop remaining degree | Finger print removal properties | Water drop remaining degree |
| Example 1 | good | 75° | 113° | A | A | B | A |
| Comparative Example 1 | good | 5° | 9° | C | D | C | D |

Examples 2 to 7 and Comparative Examples 2 to 4

Treating solutions were prepared in the same manner as in Example 1 except that instead of compound (a-1) used in Example 1, the compounds as identified in Table 2 were used in the amounts (g) as identified in Table 2, and using the treating solutions, sample glasses were prepared and evaluated in the same manner as in Example 1. The evaluation results are shown in Table 3.

TABLE 2

| Compounds | a-3 | a-4 | b-1 | b-2 | b-3 |
|---|---|---|---|---|---|
| Example 2 | | 2.0 | | | |
| Example 3 | 1.0 | | 1.0 | | |
| Example 4 | 1.8 | | 0.2 | | |
| Example 5 | 0.2 | | 1.8 | | |
| Example 6 | 1.0 | | 0.5 | | 0.5 |
| Example 7 | | 1.0 | | 1.0 | |
| Comparative Example 2 | | | 2.0 | | |
| Comparative Example 3 | | | | 2.0 | |
| Comparative Example 4 | | | | | 2.0 |

Compound (a-3): $(C_8F_{17}C_2H_4)(OCN)_2SiOSi(C_8F_{17}C_2H_4)(NCO)_2$
Compound (a-4): $(C_8F_{17}C_2H_4)(OCN)_2SiOSi(NCO)_3$
Compound (b-1): $C_8F_{17}C_2H_4Si(NCO)_3$
Compound (b-2): $C_{18}H_{37}Si(NCO)_3$
Compound (b-3): $Si(NCO)_4$ CR39 polymer (CR) or an aluminum plate (AL) was used as the substrate, and the sample was evaluated in the same manner as in Example 1. The results are shown in Table 4.

Comparative Examples 5 to 8

The same treatment as in Comparative Example 1 was carried out except that instead of the glass plate used in Comparative Example 1, an acrylic plate (AC), a polycarbonate plate (PC), a plate of CR39 polymer (CR) or an aluminum plate (AL) was used as the substrate, and the sample was evaluated in the same manner as in Comparative Example 1. The results are shown in Table 4.

TABLE 3

| | Appearance | Antifouling properties | | | | Antifouling durability | |
|---|---|---|---|---|---|---|---|
| | | Contact angle Hexadecane | Contact angle Water | Finger print removal properties | Water drop remaining degree | Finger print removal properties | Water drop remaining degree |
| Example 2 | good | 70° | 111° | A | A | B | A |
| Example 3 | good | 75° | 110° | A | A | B | A |
| Example 4 | good | 73° | 110° | A | A | B | A |
| Example 5 | good | 73° | 110° | A | A | B | B |
| Example 6 | good | 76° | 113° | A | A | B | A |
| Example 7 | good | 61° | 108° | A | A | B | A |
| Comparative Example 2 | good | 77° | 110° | A | A | B | B |
| Comparative Example 3 | good | 34° | 102° | B | A | C | B |
| Comparative Example 4 | good | 11° | 27° | C | D | C | D |

EXAMPLES 8 to 11

The same treatment as in Example 1 was carried out except that instead of the glass plate used in Example 1, an acrylic plate (AC), a polycarbonate plate (PC), a plate of

TABLE 4

| | Substrate | Antifouling properties | | | | Antifouling durability | |
|---|---|---|---|---|---|---|---|
| | | Contact angle Hexadecane | Contact angle Water | Finger print removal properties | Water drop remaining degree | Finger print removal properties | Water drop remaining degree |
| Example 8 | AC | 74° | 113° | A | A | B | A |
| Example 9 | PC | 73° | 111° | A | A | B | A |
| Example 10 | CR | 74° | 112° | A | A | B | A |
| Example 11 | AL | 77° | 115° | A | A | B | A |
| Comparative | AC | 21° | 61° | C | D | C | D |

TABLE 4-continued

| | | Antifouling properties | | | | Antifouling durability | |
|---|---|---|---|---|---|---|---|
| | Substrate | Contact angle Hexadecane | Contact angle Water | Finger print removal properties | Water drop remaining degree | Finger print removal properties | Water drop remaining degree |
| Example 5 Comparative Example 6 | PC | 34° | 72° | C | C | C | D |
| Comparative Example 7 | CR | 10° | 66° | C | D | C | D |
| Comparative Example 8 | AL | 46° | 76° | C | C | C | D |

EXAMPLES 12 to 14

The sample glass of Example 1 was heat-treated at 100° C., 200° C. and 300° C., and evaluated in the same manner as in Example 1. The results are shown in Table 5.

TABLE 5

| | | Antifouling properties | | | | Antifouling durability | |
|---|---|---|---|---|---|---|---|
| | Treating temp. °C. | Contact angle Hexadecane | Contact angle Water | Finger print removal properties | Water drop remaining degree | Finger print removal properties | Water drop remaining degree |
| Example 12 | 100 | 73° | 113° | A | A | B | A |
| Example 13 | 200 | 73° | 111° | A | A | B | A |
| Example 14 | 300 | 72° | 112° | A | A | B | A |

EXAMPLE 15

Into a three-necked flask equipped with a stirrer and a thermometer, 0.1 g of Si(NCO)$_4$ and 99.9 g of ethyl acetate were introduced and stirred for one hour. While maintaining the temperature of this solution at 25° C., stirring was continued for one day to obtain treating agent 15.

1 cc of the solution of treating agent 15 was dropped on a glass plate (10 cm×10 cm×3 mm in thickness) which was preliminarily cleaned by polishing with cerium oxide, and spread by a JK wiper in a manner similar to waxing an automobile. This plate was left to stand for one hour in an environment with a humidity of 50%. Then, on the treated surface, 1 cc of the solution of treating agent 1 was dropped, and spread by a JK wiper likewise in a manner similar to waxing an automobile. This plate was left to stand one day in an environment with a humidity of 50% to obtain a test specimen. This test specimen was evaluated in the same manner as in Example 1, and the results are shown in Table 6.

EXAMPLE 16

Into a three-necked flask equipped with a stirrer and a thermometer, 0.1 g of Si(NCO)$_4$, 0.1 g of (NCO)$_3$SiC$_2$H$_4$Si(NCO)$_3$ and 99.8 g of ethyl acetate were introduced and stirred for one hour. While maintaining the temperature of this solution at 25° C., stirring was continued for one day to obtain treating agent 16.

The test and evaluations were carried out in the same manner as in Example 15 except that treating agent 15 used in Example 15 was changed to treating agent 16. The results are also shown in Table 6.

EXAMPLE 17

Into a container equipped with a stirrer and a thermometer, 605.3 g hexylene glycol was introduced. Then, 43.8 g of Si(OC$_2$H$_5$)$_4$ and 43.7 g of a 1 wt % hydrochloric acid aqueous solution were sequentially added thereto, and stirring was carried out at 30° C. for 30 minutes. Then, the mixture was left to stand for one day to obtain treating agent 17.

Treating agent 17 was coated by a flexo printing method on a glass plate (10 cm×10 cm×3 mm in thickness) which was preliminarily cleaned by polishing with cerium oxide, and then heat-treated at 600° C. for 10 minutes in a muffle furnace. After the heat treatment, the plate was taken out from the muffle furnace and cooled to room temperature. Then, on the treated surface of this plate, 1 cc of treating agent 1 was dropped and spread by a JK wiper (manufactured by Jujo Kimberly K.K.) in a manner similar to waxing an automobile. This plate was left to stand for one day in an environment at 25° C. with a humidity of 50% to obtain a test specimen. This test specimen was evaluated in the same manner as in Example 1, and the results are shown in Table 6.

EXAMPLE 18

Into a container equipped with a stirrer and a thermometer, 605.3 g of hexylene glycol was introduced. Then, 43.8 g of Si(OC$_2$H$_5$)$_4$, 43.7 g of a 1 wt % hydrochloric acid aqueous solution and 30.0 g of fine particles of polystyrene having an average particle size of 70 nm were sequentially added thereto, and stirring was carried out at 30° C. for 30 minutes. Then, the mixture was left to stand for one day to obtain treating agent 18.

The subsequent operation was conducted in the same manner as in Example 17 except that instead of treating agent 17 used in Example 17, treating agent 18 was used, and the evaluations were carried out in the same manner as in Example 17. The results are shown in Table 6.

EXAMPLE 19

Into a container equipped with a stirrer and a thermometer, 605.3 g of hexylene glycol was introduced. Then, 43.8 g of $Si(OC_2H_5)_4$, 43.7 g of a 1 wt % hydrochloric acid aqueous solution and 7.0 g of fine particles of polymethyl methacrylate having an average particle size of 150 nm were sequentially added thereto, and stirring was carried out at 30° C. for 30 minutes. The mixture was left to stand for one day to obtain treating agent 19.

The subsequent operation was conducted in the same manner as in Example 17 except that instead of treating agent 17 used in Example 17, treating agent 19 was used, and the evaluations were carried out in the same manner as in Example 17. The results are shown in Table 6.

EXAMPLE 20

Into a container equipped with a stirrer and a thermometer, 605.3 g of hexylene glycol was introduced. Then, 43.8 g of $Si(OC_2H_5)_4$, 43.7 g of a 1 wt % hydrochloric acid aqueous solution and 28.0 g of a dispersion of fine particles of polymethyl methacrylate having an average particle size of 80 nm (MS-300, tradename, manufactured by Soken Kagaku K.K.) were sequentially added thereto, and stirring was carried out at 30° C. for 30 minutes. The mixture was left to stand for one day to obtain treating agent 20.

The subsequent operation was conducted in the same manner as in Example 17 except that instead of treating agent 17 used in Example 17, treating agent 20 was used, and the evaluations were carried out in the same manner as in Example 17. The results are shown in Table 6.

EXAMPLE 21

Into a container equipped with a stirrer and a thermometer, 935.0 g of isobutyl acetate was introduced. Then, 25.0 g of $Si(NCO)_4$ and 40.0 g of a dispersion of fine particles of polymethyl methacrylate having an average particle size of 80 nm (MS-300, tradename, manufactured by Soken Kagaku K.K.) were sequentially added thereto, and stirring was carried out at 30° C. for 30 minutes. The mixture was left to stand for one day to obtain treating agent 21.

The subsequent operation was conducted in the same manner as in Example 17 except that instead of treating agent 17 used in Example 17, treating agent 21 was used, and the evaluations were carried out in the same manner as in Example 17. The results are shown in Table 6.

Comparative Example 9

Into a three-necked flask equipped with a stirrer and a thermometer, 2.0 g of $C_8F_{17}C_2H_4Si(NCO)_3$ and 98.0 g of ethyl acetate were introduced and stirred for one hour. While maintaining the temperature of this solution at 25° C., stirring was continued for one day to obtain treating agent 22. The test and evaluations were carried out in the same manner as in Example 15 except that treating agent 1 used in Example 15 was changed to treating agent 22. The results are also shown in Table 6.

Comparative Example 10

The test and evaluations were carried out in the same manner as in Example 20 except that the treating agent 1 used in Example 20 was changed to treating agent 22. The results are also shown in Table 6.

Comparative Example 11

Into a three-necked flask equipped with a stirrer and a thermometer, 2.5 g of $C_8F_{17}C_2H_4Si(OCH_3)_3$ and 72.0 g of isopropyl alcohol were introduced and stirred for one hour. To this solution, 0.7 g of a 1 wt % hydrochloric acid aqueous solution was dropwise added over a period of one hour. While maintaining the temperature of this solution at 25° C., stirring was continued for 3 days to obtain treating agent 23.

1 cc of the solution of treating agent 15 was dropped on a glass plate (10 cm×10 cm×3 mm in thickness) which was preliminarily cleaned by polishing with cerium oxide, and spread by a JK wiper in a manner similar to waxing an automobile. This plate was left to stand for one hour in an environment with a humidity of 50% at 25° C. Then, on the treated surface, 1 cc of the solution of treating agent 23 was dropped, and spread by a JK wiper likewise in a manner similar to waxing an automobile, followed by heat drying at 100° C. for 30 minutes to obtain a test specimen. This test specimen was evaluated in the same manner as in Example 15, and the results are shown in Table 6.

Comparative Example 12

Treating agent 20 was coated by a flexo printing method on a glass plate (10 cm×10 cm×3 mm in thickness) which was preliminarily cleaned by polishing with cerium oxide, and heat-treated at 600° C. for 10 minutes in a muffle furnace. After the heat treatment, the plate was taken out from the muffle furnace and cooled to room temperature. Then, on the treated surface of this plate, 1 cc of treating agent 23 was dropped, and spread by a JK wiper (manufactured by Jujo Kimberly K.K.) in a manner similar to waxing an automobile, followed by heat drying at 100° C. for 30 minutes to obtain a test specimen. This test specimen was evaluated in the same manner as in Example 15, and the results are shown in Table 6.

TABLE 6

|  | Appearance | Antifouling properties ||||| Antifouling durability ||
| --- | --- | --- | --- | --- | --- | --- | --- |
|  |  | Contact angle Hexadecane | Contact angle Water | Finger print removal properties | Water drop remaining degree | Finger print removal properties | Water drop remaining degree |
| Example 15 | good | 72° | 112° | A | A | A | A |
| Example 16 | good | 72° | 112° | A | A | A | A |

TABLE 6-continued

| | Antifouling properties | | | | | Antifouling durability | |
|---|---|---|---|---|---|---|---|
| | Appearance | Contact angle Hexadecane | Contact angle Water | Finger print removal properties | Water drop remaining degree | Finger print removal properties | Water drop remaining degree |
| Example 17 | good | 71° | 113° | A | A | A | A |
| Example 18 | good | 73° | 116° | A | A | A | A |
| Example 19 | good | 76° | 118° | A | A | A | A |
| Example 20 | good | 76° | 118° | A | A | A | A |
| Example 21 | good | 74° | 114° | A | A | A | A |
| Comparative Example 9 | good | 75° | 112° | A | A | B | B |
| Comparative Example 10 | good | 75° | 112° | A | A | B | A |
| Comparative Example 11 | good | 69° | 104° | A | A | C | B |
| Comparative Example 12 | good | 70° | 108° | A | A | C | B |

EXAMPLE 22

The sample glass of Example 1 was immersed in a reagent as identified in Table 7 for 24 hours, and it was taken out and immediately washed, whereupon the change in the appearance of this sample, the finger print removal properties and water drop remaining degree were evaluated. The results are shown in Table 7.

EXAMPLE 23

The test and evaluations were carried out in the same manner as in Example 22 except that instead of the sample glass of Example 1 used in Example 22, the sample glass of Example 15 was used. The results are shown in Table 7.

EXAMPLE 24

The test and evaluations were carried out in the same manner as in Example 22 except that instead of the sample glass of Example 1 used in Example 22, the sample glass of Example 17 was used. The results are shown in Table 7.

EXAMPLE 25

The test and evaluations were carried out in the same manner as in Example 22 except that instead of the sample glass of Example 1 used in Example 22, the sample glass of Example 20 was used. The results are shown in Table 7.

TABLE 7

| Examples | Reagent | Appearance | Finger print removal properties | Water drop remaining degree |
|---|---|---|---|---|
| Example 22 | Methanol | No change | A | A |
| | Acetone | No change | A | A |
| | 1% Sulfuric acid aqueous solution | No change | A | A |
| | 1% Sodium hydroxide aqueous solution | No change | A | A |
| | Gasoline | No change | A | A |
| Example 23 | Methanol | No change | A | A |
| | Acetone | No change | A | A |
| | 1% Sulfuric acid aqueous solution | No change | A | A |
| | 1% Sodium hydroxide aqueous solution | No change | A | A |
| | Gasoline | No change | A | A |
| Example 24 | Methanol | No change | A | A |
| | Acetone | No change | A | A |
| | 1% Sulfuric acid aqueous solution | No change | A | A |
| | 1% Sodium hydroxide aqueous solution | No change | A | A |
| | Gasoline | No change | A | A |
| Example 25 | Methanol | No change | A | A |
| | Acetone | No change | A | A |
| | 1% Sulfuric acid aqueous solution | No change | A | A |
| | 1% Sodium hydroxide aqueous solution | No change | A | A |
| | Gasoline | No change | A | A |

EXAMPLE 26

To the sample glass of Example 1, reciprocal abrasion of 20,000 times with a flannel cloth was applied with a load of 1 kg. After the abrasion test, the antifouling properties were evaluated, and the results are shown in Table 8.

Comparative Example 13

The abrasion test and the evaluation were carried out in the same manner as in Example 26 except that instead of the sample glass of Example 1 used in Example 26, the sample glass of Comparative Example 2 was used. The results are shown in Table 8.

EXAMPLE 27

The abrasion test and the evaluation were carried out in the same manner as in Example 26 except that instead of the sample glass of Example 1 used in Example 26, the sample glass of Example 15 was used. The results are shown in Table 8.

EXAMPLE 28

The abrasion test and the evaluation were carried out in the same manner as in Example 26 except that instead of the sample glass of Example 1 used in Example 26, the sample glass of Example 17 was used. The results are shown in Table 8.

EXAMPLE 29

The abrasion test and the evaluation were carried out in the same manner as in Example 26 except that instead of the sample glass of Example 1 used in Example 26, the sample glass of Example 20 was used. The results are shown in Table 8.

EXAMPLE 31

The test and the evaluation were carried out in the same manner as in Example 30 except that instead of the sample glass of Example 1 used in Example 30, the sample glass of Example 15 was used. The results are shown in Table 9.

EXAMPLE 32

The test and the evaluation were carried out in the same manner as in Example 30 except that instead of the sample glass of Example 1 used in Example 30, the sample glass of Example 17 was used. The results are shown in Table 9.

EXAMPLE 33

The test and the evaluation were carried out in the same manner as in Example 30 except that instead of the sample glass of Example 1 used in Example 30, the sample glass of Example 20 was used. The results are shown in Table 9.

TABLE 8

|  | Appearance | Contact angle Hexadecane | Contact angle Water | Finger print removal properties | Water drop remaining degree |
|---|---|---|---|---|---|
| Example 26 | good | 54° | 80° | B | B |
| Comparative Example 13 | good | 33° | 54° | C | C |
| Example 27 | good | 60° | 95° | A | A |
| Example 28 | good | 56° | 89° | B | B |
| Example 29 | good | 68° | 104° | A | A |

EXAMPLE 30

A weather resistant test in which a process comprising ultraviolet irradiation for 8 hours (70° C.) and humidity exposure for 4 hours (50° C.) was regarded as one cycle, was carried out for 25 cycles against the sample glass of Example 1. After the weather resistant test, the antifouling properties were evaluated, and the results are shown in Table 9.

Comparative Example 14

The test and the evaluation were carried out in the same manner as in Example 30 except that instead of the sample glass of Example 1 used in Example 30, the sample glass of Comparative Example 2 was used. The results are shown in Table 9.

TABLE 9

|  | Appearance | Contact angle Hexadecane | Contact angle Water | Finger print removal properties | Water drop remaining degree |
|---|---|---|---|---|---|
| Example 30 | good | 55° | 80° | B | B |
| Comparative Example 14 | good | 44° | 74° | C | B |
| Example 31 | good | 60° | 96° | B | A |
| Example 32 | good | 54° | 88° | B | B |
| Example 33 | good | 68° | 101° | A | A |

EXAMPLE 34

The surface of a laminated front glass for an automobile was treated in the same manner as in Example 1, and the front glass was mounted on an automobile. This automobile was subjected to a running test of four hours per day for one month, whereby deposition of soil or dust on the surface of the front glass was visually observed every day, and deposition of water droplets was visually observed when it rained.

As a result, no deposition of soil or dust and no formation of fur due to deposition of water droplets was observed, and even when observed, such deposition or formation was readily removed by gentle wiping with a tissue paper. Further, at the time of raining, water drops on the surface were repelled and readily moved away by an interaction with wind pressure by running, whereby the visual field was secured without using a wiper. Further, in a running test under an environment (0° C. to −5° C.) underwhich water drops deposited on a non-treated laminated front glass would freeze or underwhich moisture in air would condense and frost on a front glass, no freezing or frosting on the front glass was observed.

Then, under a severer low temperature environment (−10° C. to −15° C.), frosting was observed on the front glass, but the defrosting was quick, and there was a remarkable difference from the non-treated front glass.

EXAMPLE 35

The running test was carried out in the same manner as in Example 34 except that the laminated front glass of Example 34 was changed to a side glass, a rear glass or a side mirror, whereby the same effects as in Example 34 were confirmed.

EXAMPLE 36

The running test was carried out in the same manner as in Example 34 except that instead of the treating method of Example 1 used in Example 34, the treating method of Example 15 was used, whereby the same effects as in Example 34 were confirmed.

EXAMPLE 37

The running test was carried out in the same manner as in Example 34 except that instead of the treating method of Example 1 used in Example 34, the treating method of Example 20 was used, whereby the same effects as in Example 34 were confirmed.

EXAMPLE 38

The surface of a window glass for building was treated in the same manner as in Example 1 to form a coating film. The window glass thus obtained was attached to a house. Deposition of soil and dust on the surface of this window glass as well as deposition of water droplets when it rained, were visually observed.

As a result, no deposition of soil or dust, or no formation of fur due to deposition of water droplets was observed, and if observed, such deposition or formation was readily removed by gently wiping with tissue paper. Further, at the time of raining, water drops on the surface were repelled and fell off, and especially when a strong wind blew, water drops were readily moved away by the interaction with the wind pressure, whereby visual field was secured. Further, in a test in an environment (0° C. to −5° C.) underwhich water droplets deposited on a non-treated window glass would freeze, or moisture in air would condense and frost on a window glass, no freezing or frosting on the window glass was observed.

Then, under a severer low temperature environment (−10° C. to −15° C.), frosting on the window glass was observed, but defrosting was quick, and there was a remarkable difference as compared with the non-treated window glass.

EXAMPLE 39

The laminated front glass of an automobile glass used for more than 5 years, was polished with calcium carbonate, washed with water and dried. Then, 10 cc of the solution of treating agent 1 was dropped on the laminated front glass surface and spread by a JK wiper in a manner similar to waxing an automobile.

Using this automobile, a running test was carried out in the same manner as in Example 34, whereby the same effects as in Example 34 were confirmed.

EXAMPLE 40

The laminated front glass of an automobile glass used for more than 5 years, was polished with calcium carbonate, washed with water and dried. Then, 10 cc of the solution of treating agent 15 was dropped on the laminated front glass surface, then spread by a JK wiper in a manner similar to waxing an automobile, and left to stand for one hour at 19° C. under a humidity of 46%. Then, 10 cc of the solution of treating agent 1 was dropped on the treated surface, then spread by a JK wiper in a manner similar to waxing an automobile and left to stand for one day.

Using this automobile, a running test was carried out in the same manner as in Example 34, whereby the same effects as in Example 34 were confirmed.

The treating agent of the present invention, a substrate having a coating film obtained from the surface treating agent and an article provided therewith have the following excellent effects.

(1) The surface treating agent of the present invention is useful for normal temperature treatment and capable of imparting excellent antifouling properties to a substrate. Accordingly, it is useful not only for treatment of an article produced anew but also for treatment of an article which has already been used. Further, it requires no heat treatment, whereby it may be applied to a necessary portion without deforming the shape of the article to be treated.

(2) The substrate of the present invention or an article provided therewith is excellent in antifouling properties and is free from deposition of dust, soil or water drops or formation of fur due to such deposition. Even if observed, such deposition or formation can readily be removed, whereby adverse effects resulting from water can be prevented, and cleaning operation can be simplified.

(3) The substrate of the present invention or an article provided therewith has excellent antifouling properties and at the same time has chemical resistance, abrasion resistance and weather resistance, whereby it is excellent in durability of the antifouling properties, and the antifouling properties can be maintained semipermanently.

(4) The surface treating agent of the present invention can be applied not only to glass but also to a wide range of other substrates. Further, no special pretreatment is required for its application, and continuous treatment is possible. Therefore, it is also advantageous from the economical viewpoint.

The above effects can not be expected with conventional materials, and the present invention is expected to be applicable in an area where the conventional materials could not be practically used.

What is claimed is:

1. A surface treating agent containing a silicone compound of the formula (A):

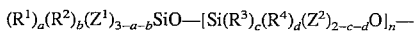

$$Si(R^5)_e(R^6)_f(Z^3)_{3-e-f} \quad (A)$$

wherein each of $R^1$ to $R^6$ which are independent of one another, is a hydrogen atom or an organic group attached to Si through a carbon atom, provided that at least one of $R^1$ to $R^6$ is an organic group;

each of $Z^1$ to $Z^2$ which are independent of one another, is an isocyanate group or a hydrolyzable group, wherein at least one of $Z^1$ to $Z^3$ in the formula (A) is an isocyanate group;

each of a to f which are independent of one another, is an integer of 0, 1 or 2, provided $1 \leq a+b \leq 3$, $0 \leq c+d \leq 2$, $1 \leq e+f \leq 3$ and $2 \leq a+b+c+d+e+f \leq 7$; and n is an integer of 0 or at least 1.

2. The surface treating agent according to claim 1, wherein the silicone compound is a silicone compound of the formula (A2):

$$(R_f^1)(OCN)_2SiOSi(R_f^2)(NCO)_2 \quad (A2)$$

wherein each of $R_f^1$ and $R_f^2$ which are independent of each other is a polyfluoroorganic group.

3. The surface treating agent according to claim 1, wherein the silicone compound is a silicone compound of the formula (A3):

$$(R_f^3)(OCN)_2SiOSi(NCO)_3 \quad (A3)$$

wherein $R_f^3$ is a polyfluoroorganic group.

4. The surface treating agent according to claim 1, which further contains a compound of the formula (B):

$$(R^7)_p(R^8)_q(R^9)_r Si(NCO)_{4-p-q-r} \quad (B)$$

wherein each of $R^7$ to $R^9$ which are independent of one another, is a hydrogen atom or a $C_{1-30}$ organic group; and each of p, q and r which are independent of one another, is an integer of 0, 1, 2 or 3, provided $0 \leq p+q+r \leq 3$.

5. A substrate having its surface treated with the surface treating agent as defined in claim 1.

6. A substrate having at least two treated surface layers, wherein the first layer constituting the outermost layer among the treated surface layers is a layer formed by treatment with the surface treating agent of claim 1, and the second layer constituting an underlayer in contact with the outermost layer is a layer formed by treatment with a treating agent containing a compound (C) capable of forming a thin film of a heat-resistant polymer.

7. A substrate having at least two treated surface layers, wherein the first layer constituting the outermost layer among the treated surface layers is a layer formed by treatment with the surface treating agent of claim 1, and the second layer constituting an underlayer in contact with the outermost layer is a layer formed by treating the substrate surface with a treating agent containing a compound (C) capable of forming a thin film of a heat-resistant polymer and fine particles of a polymer, to form a thin film and heating the thin film to thermally decompose the fine particles of a polymer.

8. The substrate according to claim 7, wherein the average particle size of the fine particles of a polymer is from 1 to 1000 nm.

9. The substrate according to claim 6, wherein compound (C) is a reactive silane compound having an isocyanate group and/or a hydrolyzable group bonded to a silicon atom.

10. The substrate according to claim 6, wherein compound (C) is a compound of the following formula (C1) and/or (c2):

$$(Z)_{3-i-j}(R^{10})_i(R^{11})_j Si-Y-Si(R^{12})_k(R^{13})_m(Z)_{3-k-m} \quad (C1)$$

wherein each of $R^{10}$, $R^{11}$, $R^{12}$ and $R^{13}$ which are independent of one another, is a hydrogen atom, a hydroxyl group, an amino group or a $C_{1-30}$ organic group;

Y is a bivalent organic group;

Z is an isocyanate group and/or a hydrolyzable group;

each of i and j which are independent of each other, is an integer of 0, 1 or 2, provided $0 \leq i+j \leq 2$; and each of k and m which are independent of each other, is an integer of 0, 1 or 2, provided $0 \leq k+m \leq 2$;

$$(R^{14})_e(R^{15})_g(R^{16})_h Si(Z)_{4-e-g-h} \quad (C2)$$

wherein each of $R^{14}$, $R^{15}$ and $R^{16}$ which are independent of one another, is a hydrogen atom or a $C_{1-30}$ organic group, provided that at least one of $R^{14}$, $R^{15}$ and $R^{16}$ is the organic group;

Z is an isocyanate group and/or a hydrolyzable group; and each of e, g and h which are independent of one another, is an integer of 0, 1 or 2, provided $0 \leq e+g+h \leq 3$.

11. The substrate according to claim 6, wherein compound (C) is a tetraisocyanate silane and/or a tetraalkoxysilane.

12. The substrate according to claim 6, wherein the treating agent containing compound (C) is one containing a metal and/or a metal oxide.

13. The substrate according to claim 7, wherein compound (C) is a reactive silane compound having an isocyanate group and/or a hydrolyzable group bonded to a silicon atom.

14. The substrate according to claim 7, wherein compound (C) is a compound of the following formula (C1) and/or (c2):

$$(Z)_{3-i-j}(R^{10})_i(R^{11})_j Si-Y-Si(R^{12})_k(R^{13})_m(Z)_{3-k-m} \quad (C1)$$

wherein each of $R^{10}$, $R^{11}$, $R^{12}$ and $R^{13}$ which are independent of one another, is a hydrogen atom, a hydroxyl group, an amino group or a $C_{1-30}$ organic group;

Y is a bivalent organic group;

Z is an isocyanate group and/or a hydrolyzable group;

each of i and j which are independent of each other, is an integer of 0, 1 or 2, provided $0 \leq i+j \leq 2$; and each of k and m which are independent of each other, is an integer of 0, 1 or 2, provided $0 \leq k+m \leq 2$;

$$(R^{14})_e(R^{15})_g(R^{16})_h Si(Z)_{4-e-g-h} \quad (C2)$$

wherein each of $R^{14}$, $R^{15}$ and $R^{16}$ which are independent of one another, is a hydrogen atom or a $C_{1-30}$ organic group, provided that at least one of $R^{14}$, $R^{15}$ and $R^{16}$ is the organic group;

Z is an isocyanate group and/or a hydrolyzable group; and each of e, g and h which are independent of one another, is an integer of 0, 1 or 2, provided $0 \leq e+g+h \leq 3$.

15. The substrate according to claim 7, wherein compound (C) is a tetraisocyanate silane and/or a tetraalkoxysilane.

16. The substrate according to claim 7, wherein the treating agent containing compound (C) is one containing a metal and/or a metal oxide.

17. A process for producing a substrate having at least two treated surface layers, which comprises treating the surface of a substrate with a treating agent containing a compound (C) capable of forming a thin film of a heat-resistant polymer to form a thin film, heating the thin film, to form a thin film layer of a heat-resistant polymer, and then treating the surface of the thin film layer of a heat-resistant polymer with the surface treating agent as defined in claim 1.

18. A process for producing a substrate having at least two treated surface layers, which comprises treating the surface of a substrate with a treating agent containing a compound (C) capable of forming a thin film of a heat-resistant polymer and fine particles of a polymer, to form a thin film, heating the thin film to thermally decompose the fine particles of a polymer to form a thin film layer of a heat-resistant polymer, and then treating the surface of the thin film layer of a heat-resistant polymer with the treating agent as defined in claim 1.

* * * * *